United States Patent
Gabbay

(10) Patent No.: US 11,523,837 B2
(45) Date of Patent: Dec. 13, 2022

(54) DEVICES AND METHODS FOR A TOTALLY PERCUTANEOUS COLLAPSIBLE AORTIC PUNCH

(71) Applicant: Shlomo Gabbay, Boca Raton, FL (US)

(72) Inventor: Shlomo Gabbay, Boca Raton, FL (US)

(*) Notice: Subject to any disclaimer, the term of this patent is extended or adjusted under 35 U.S.C. 154(b) by 916 days.

(21) Appl. No.: 16/341,284

(22) PCT Filed: Oct. 11, 2017

(86) PCT No.: PCT/US2017/056091
§ 371 (c)(1),
(2) Date: Apr. 11, 2019

(87) PCT Pub. No.: WO2018/071508
PCT Pub. Date: Apr. 19, 2018

(65) Prior Publication Data
US 2019/0239904 A1    Aug. 8, 2019

Related U.S. Application Data

(63) Continuation of application No. 15/430,088, filed on Feb. 10, 2017, now abandoned, and a continuation of
(Continued)

(51) Int. Cl.
*A61B 17/22*     (2006.01)
*A61B 17/3205*   (2006.01)
(Continued)

(52) U.S. Cl.
CPC .............. *A61B 17/22* (2013.01); *A61F 2/013* (2013.01); *A61F 2/2427* (2013.01);
(Continued)

(58) Field of Classification Search
CPC .............. A61B 17/22; A61B 17/22012; A61B 17/32053; A61B 17/32075;
(Continued)

(56) References Cited

U.S. PATENT DOCUMENTS

2004/0260322 A1* 12/2004 Rudko ................... A61B 18/24
                                                     606/167
2005/0075659 A1*  4/2005 Realyvasquez ....... A61F 2/2427
                                                     606/167
(Continued)

*Primary Examiner* — Diane D Yabut

(57) ABSTRACT

A method and device for perforating an aortic valve to remove excessive calcium deposits on aortic valve leaflets improves the implantation of TAVI replacement valves in patients. By removing excessive calcium deposits, the radial pressure exerted by implanted TAVI replacement valves is reduced, such that there is less blood leakage around the valve and less stress on the cardiac conductive system. A device with a collapsible punch is inserted into the aortic valve. The punch is separable such that the aortic valve leaflets are positioned between at least two elements of the punch. The two elements then compress together with the leaflets between them, causing the aortic valve to be perforated. A circumferential ring of the remaining aortic valve and calcium deposits are left to provide stability for the TAVI replacement valve.

16 Claims, 28 Drawing Sheets

Related U.S. Application Data application No. 15/290,803, filed on Oct. 11, 2016, now abandoned.

(51) Int. Cl.
*A61B 17/3207* (2006.01)
*A61F 2/01* (2006.01)
*A61F 2/24* (2006.01)
*A61B 17/00* (2006.01)

(52) U.S. Cl.
CPC .............. *A61B 17/32053* (2013.01); *A61B 2017/00398* (2013.01); *A61B 2017/22051* (2013.01); *A61B 2017/22097* (2013.01); *A61B 2017/22098* (2013.01); *A61B 2017/320716* (2013.01); *A61F 2/2433* (2013.01); *A61F 2/2436* (2013.01); *A61F 2002/016* (2013.01); *A61F 2230/0093* (2013.01)

(58) Field of Classification Search
CPC . A61B 2017/22097; A61B 2017/22098; A61F 2/2427; A61F 2230/0093
See application file for complete search history.

(56) References Cited

U.S. PATENT DOCUMENTS

| | | | |
|---|---|---|---|
| 2008/0039881 A1* | 2/2008 | Greenberg | A61B 17/22 606/170 |
| 2008/0188880 A1* | 8/2008 | Fischer | A61B 17/320725 606/170 |
| 2009/0306691 A1* | 12/2009 | Cambronne | A61B 17/22012 606/159 |
| 2010/0168840 A1* | 7/2010 | Kassab | A61B 17/320725 623/1.26 |
| 2012/0078354 A1* | 3/2012 | Cohn | A61F 2/2427 623/2.11 |
| 2012/0253358 A1* | 10/2012 | Golan | A61B 17/221 606/128 |
| 2014/0228843 A1* | 8/2014 | O'Donnell | A61B 18/1492 606/48 |
| 2015/0238218 A1* | 8/2015 | Morales | A61B 17/320016 606/180 |

* cited by examiner

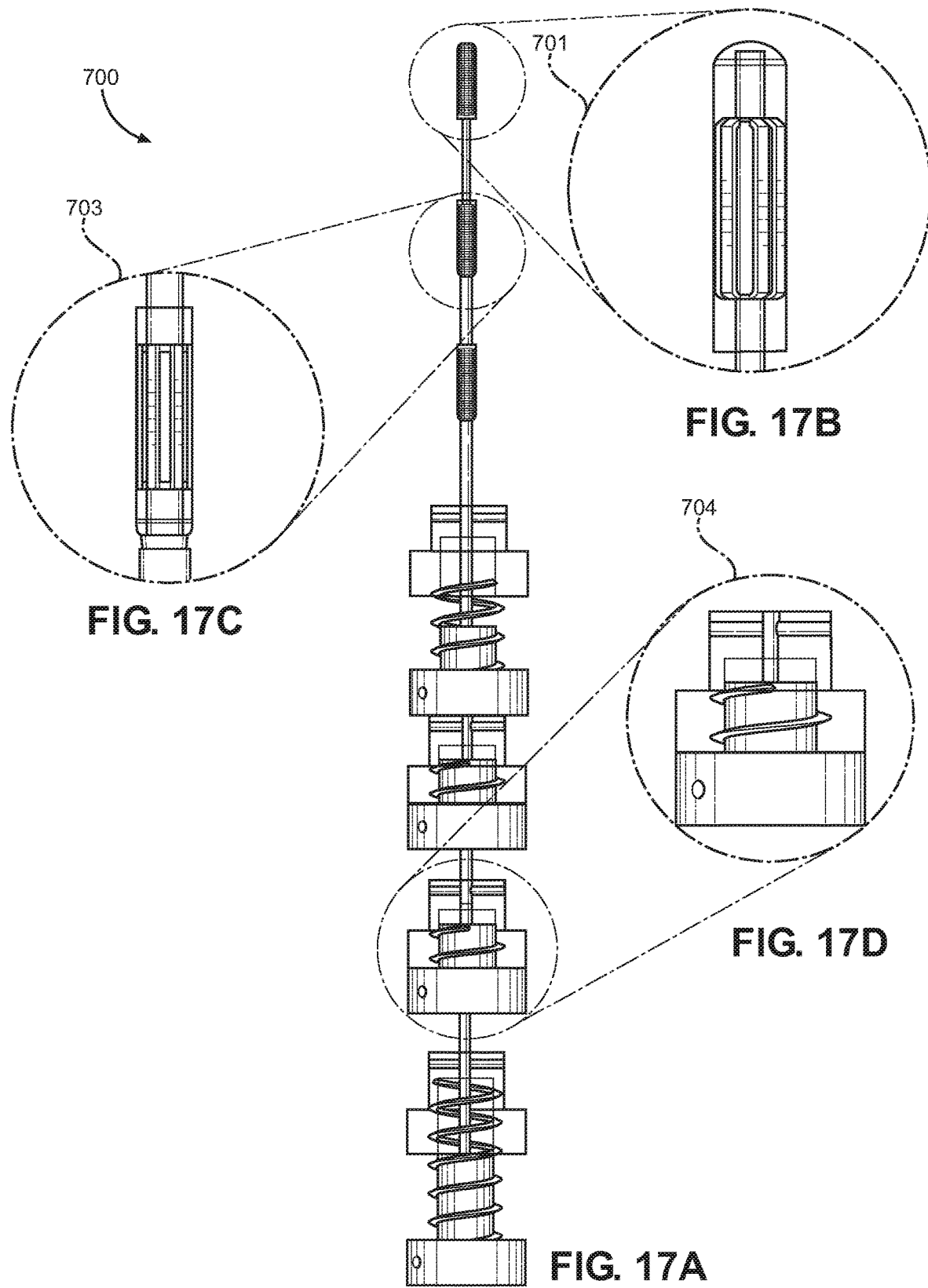

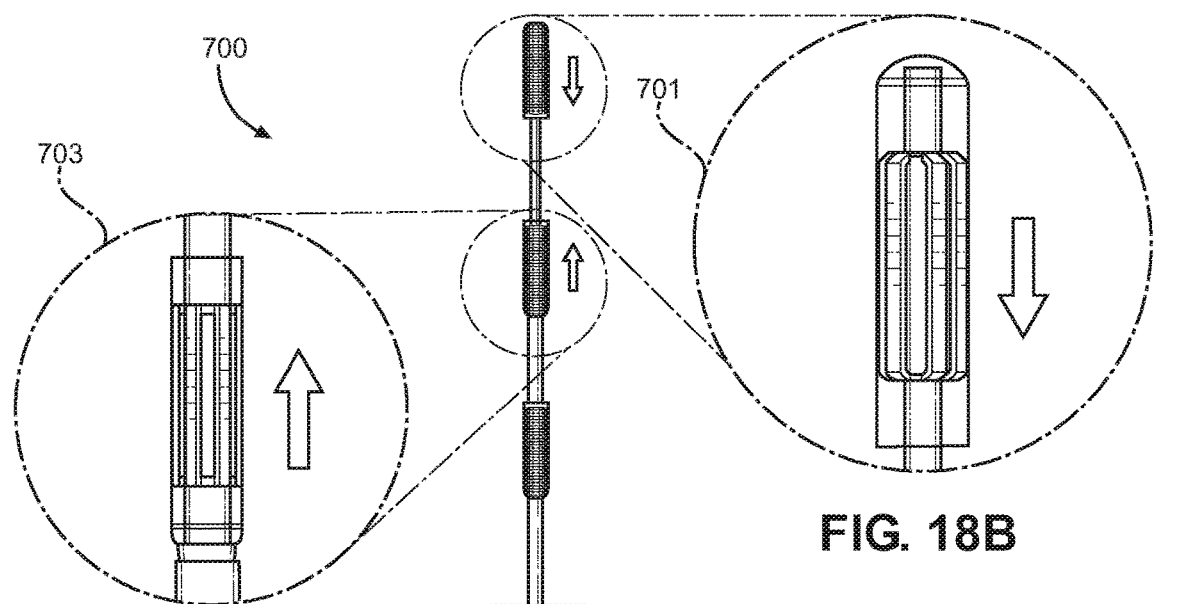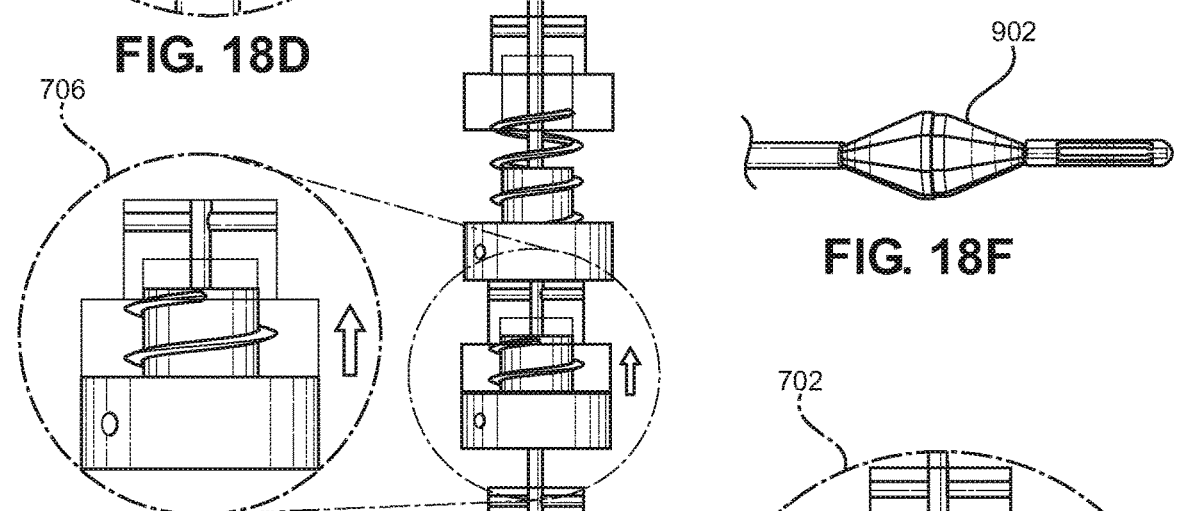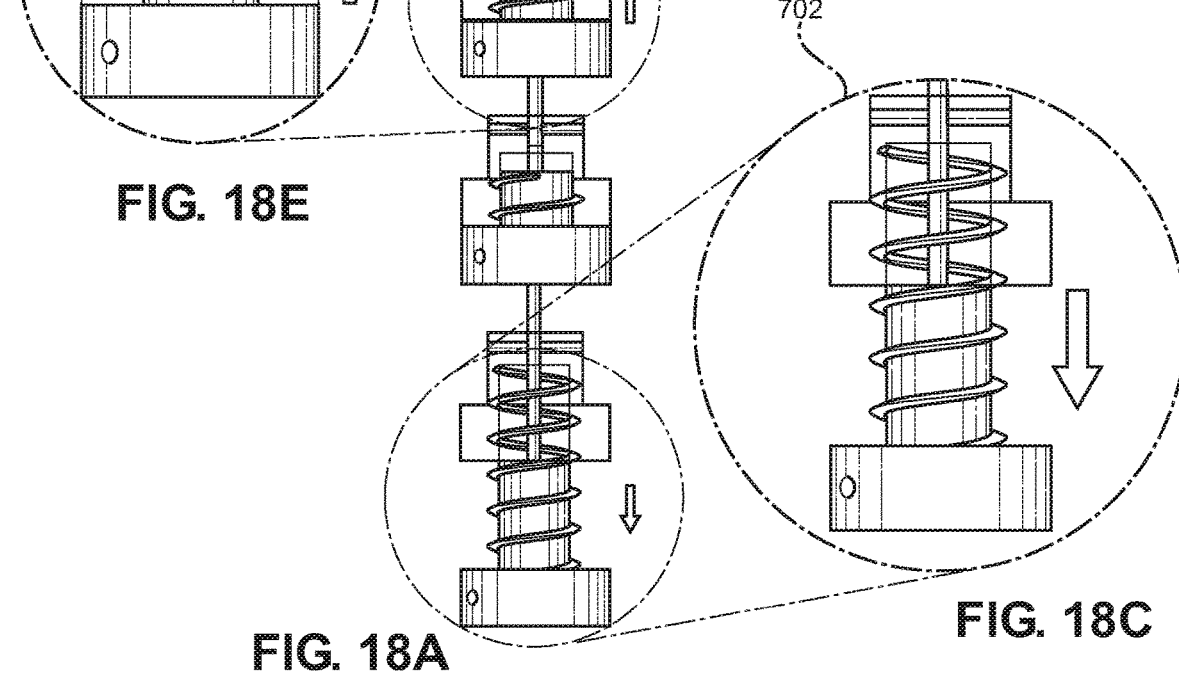

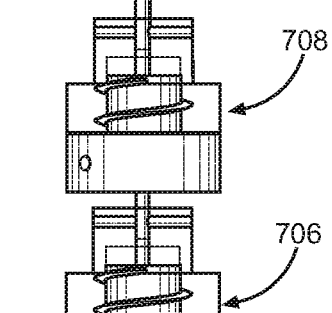
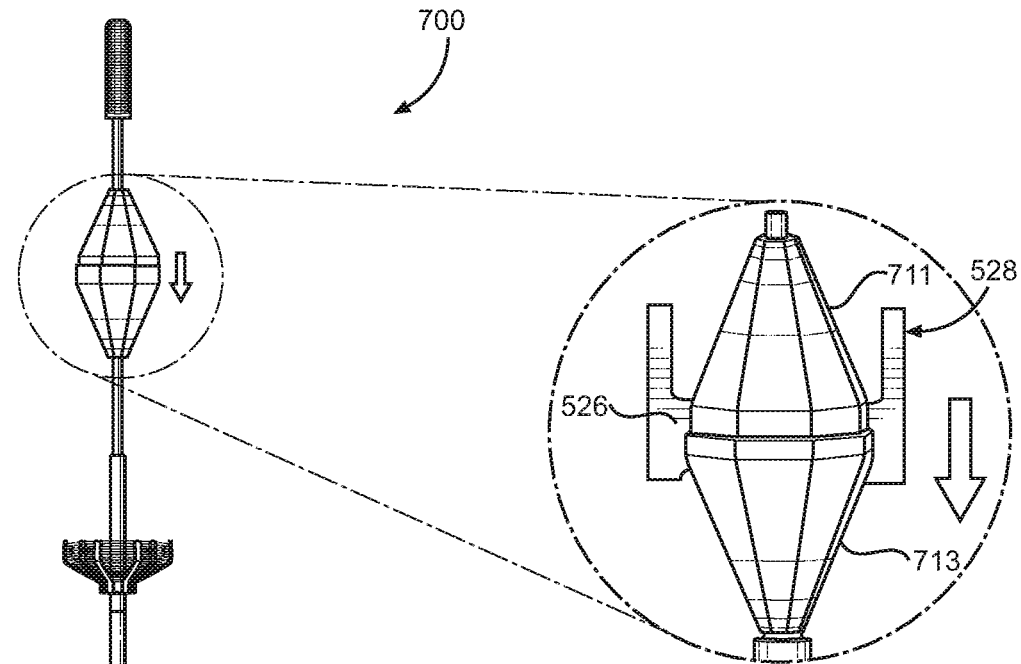
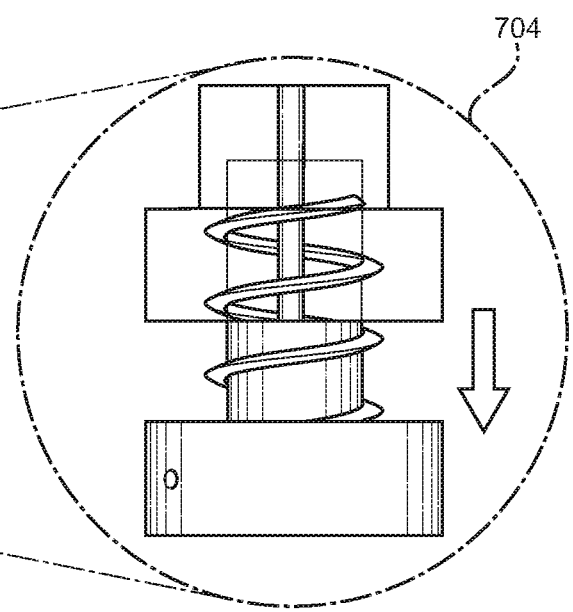
FIG. 20A
FIG. 20B
FIG. 20C

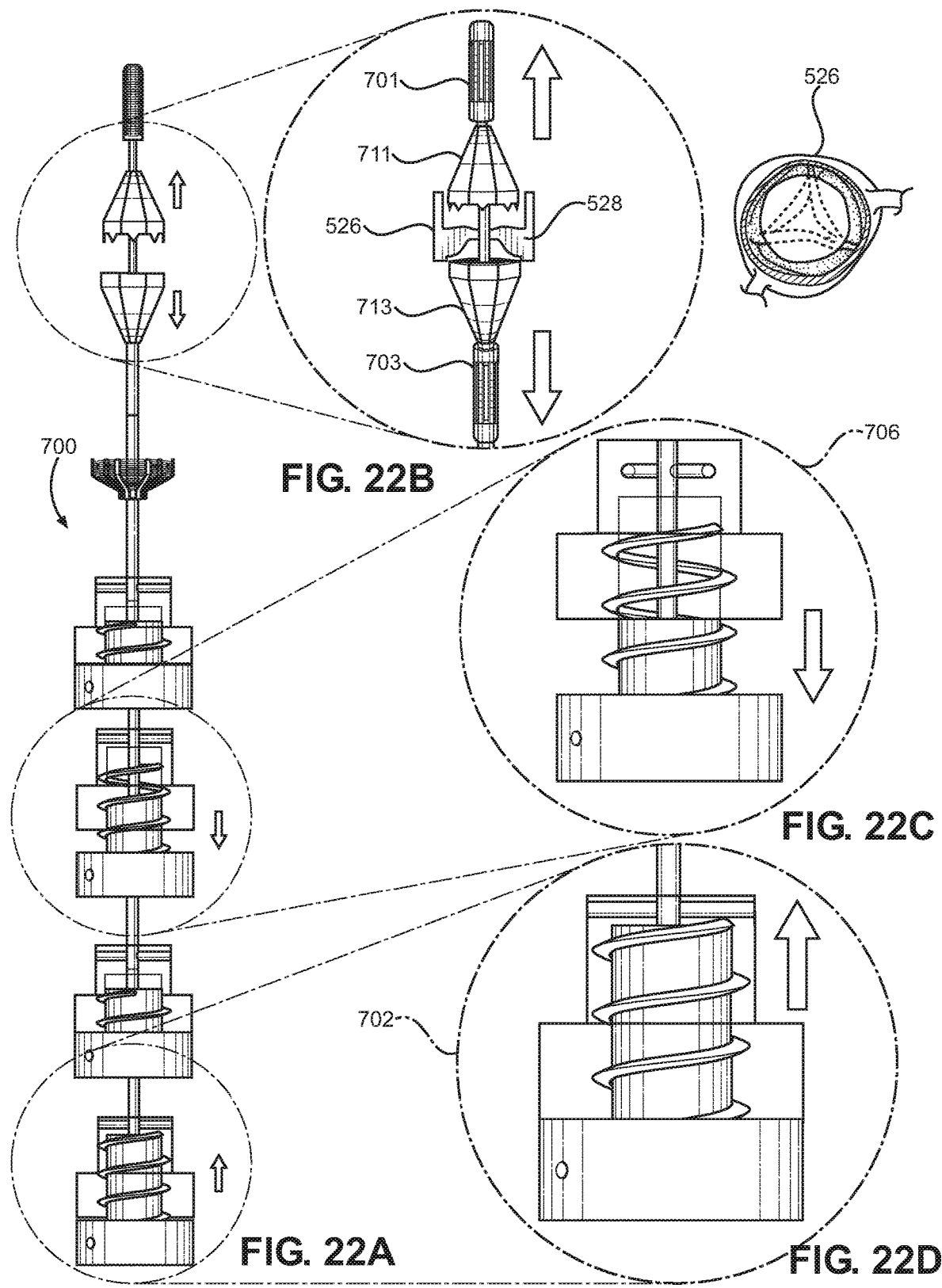

DEVICES AND METHODS FOR A TOTALLY PERCUTANEOUS COLLAPSIBLE AORTIC PUNCH

CROSS-REFERENCE TO RELATED APPLICATIONS

This application is a continuation-in-part of application Ser. No. 15/290,803, filed Oct. 11, 2016, the entire content of which is incorporated herein by reference.

TECHNICAL FIELD

The inventions described herein relate to the technical field of medical methods and devices known as Transcatheter Aortic Valve Implantation (TAVI) or Transcatheter Aortic Valve Replacements (TAVR). Specifically, the present inventions relate to methods and devices for an improved totally percutaneous collapsible aortic punch employed in TAVI.

BACKGROUND OF INVENTION

TAVI is an alternative method to traditional valve replacement. Traditionally, open-heart surgery with cardiopulmonary bypass is required to replace an aortic valve, wherein a patient's native aortic valve is surgically removed and replaced with an artificial mechanical valve. While mechanical valves were popular in the past, today about 70% of replacement valves are biological valves using biological tissue from other sources. The increased use of biological valves has increased the need for better, more effective methods of biological replacement valve implantation.

TAVI uses minimally invasive methods to replace a native aortic valve by injecting a transcatheter biological replacement valve over the native aortic valve without surgically removing the native aortic valve. A transcatheter aortic replacement valve is generally structured by a stent-like metal frame, which is collapsible and is either self-expandable or expanded by a balloon catheter. The metal frame is sutured to and supports tissue leaflets, typically bovine or porcine tissue, which act as biological valve replacements. During implantation of the replacement valve, a catheter is inserted into the aorta transfemorally, transapically, or transaortically. The catheter contains a compressed replacement valve and delivers the compressed replacement valve to the aortic valve, where the replacement valve is positioned within the aortic valve and released. The released replacement valve expands within the native aortic valve and radial pressure from the expandable metal frame situates the replacement valve within the native aortic valve by folding the leaflets against the aortic wall. Some calcification of the aortic valve leaflets is necessary to provide stability for the replacement valve and to hold the replacement valve in place.

FIG. 2A demonstrates an insertion of a catheter with a collapsed TAVI replacement valve into an aortic valve 102 using the traditional approach to the procedure. The catheter, with a contracted TAVI replacement valve coaxially attached around an outside surface is positioned within the aortic valve 102 along a guidewire. FIG. 2B shows expansion of a balloon, which expands the replacement valve within the aortic valve 102 without surgical removal of the native valve. The expansion of the balloon causes the replacement valve to fold the valve leaflets 104 upward and outward into the aorta 101, effectively sandwiching the leaflets between the aorta and replacement valve. FIG. 2C shows the resulting expanded implanted TAVI replacement valve in aortic valve, which uses only radial pressure to secure the replacement valve over the native valve 102.

Valvuloplasty is used to widen a stenotic aortic valve using a balloon catheter. The TAVI replacement valve's wire-mesh metal frame is positioned around the balloon catheter such that the balloon catheter simultaneously widens both the aortic valve and TAVI replacement valve for implantation. Therefore, correct placement of the replacement valve within the native aortic valve is crucial to long-term success of the replacement valve.

Two medical device companies have FDA-approved TAVI devices on the market. Edwards Lifesciences first introduced the SAPIEN THV, approved on Nov. 2, 2011, and has since introduced the approved SAPIEN 3 and SAPIEN XT. Medtronic produces a second type of TAVI replacement valve, the CoreValve, which was first approved on Jan. 17, 2014. As is typical of TAVI replacement valves, the SAPIEN devices and the CoreValve primarily use radial pressure to secure the replacement valve within the native valve without use of additional sutures or connections.

Based on data collected from the FDA Manufacturer and User Facility Device Experience (MAUDE) database from February 2014 to December 2015, the Edwards PARTNER Trial, and other published studies the implantation of current TAVI replacement valves requires further improvement to reduce complications and improve patient outcome. Nearly 20 percent of the FDA MAUDE complaints analyzed involved replacement valve implanting and positioning errors, including misplacement and embolization, incomplete inflation, or dislodgement of the replacement valve after implantation. Varying severities of paravalvular leaks often follow improper implantation of replacement valves in the annulus. Incomplete expansion of the replacement valve within the annulus allows high pressure blood to leak between the outer surface of replacement valve and the annulus. Depending on the patient's health, a second or third replacement valve may have to be inserted. Duplicating such procedures can increase the risk of further complications.

Further, conductive issues with the electrical conduction system of the heart can arise due to excessive radial pressure applied by the replacement valve to calcium deposits on the aortic leaflets sandwiched between the aorta and replacement valve. As shown in FIG. 1, the cardiac conduction system is crucially important because it signals distribution of oxygenated blood to the various tissues of the human body. The cardiac conduction pathway 100 begins at the sinoatrial (SA) node 105, often referred to as the pacemaker. An electrical signal travels from the SA node 105 down the atrium to the atrioventricular (AV) node 103 where it reaches the Bundle of His 108 in the interventricular septum 106. The electrical signal then splits into the left and right bundle branches 110 and 112 that travel the left and right sides of the heart. Purkinje fibers 114 derived from the left and right pathways translate the electrical signal to the cardiomuscular tissue of the heart, which contract in response causing blood to be quickly pumped out of the ventricles and out of arteries and to the rest of the body. Disruption of the electrical signal of the cardiac conduction system can interrupt cardiomuscular contractions. Critical issues can result with the heart and the rest of the body, as blood flow is interrupted or, at worst, stopped.

Traditional TAVI can exacerbate cardiac conduction system interruption in patients with TAVI replacement valves. Aortic stenosis, or the narrowing of the aortic valve 102, can be congenital or acquired and occurs when at least two of the three aortic valve leaflets 104 begin to, or are fully, fused together. FIG. 4 shows a representative sampling of various types of stenotic valves. A stenotic valve is prevented from fully opening, which in turn restricts the flow of oxygenated blood exiting the left ventricle 118. The heart must pumper harder to keep the body sufficiently oxygenated to compensate for the reduced blood flow through the aorta 101 due to a stenotic valve. This leads to hypertrophy of the left ventricle 118 and of the septum 106, which may in turn bring the conductive system closer to the implanted replacement valve. As hypertrophy of the left ventricle 118 and of the septum 106 thickens the walls of the heart, the radial pressure of a typical TAVI replacement valve applies radial force in the opposite direction and effectively squeezes the Bundle of His 108, bundle branches 110 and 112, and Purkinje fibers 114. This in turn can lead to serious cardiac complications.

Calcium build-up on the aortic valve leaflets can also cause stenosis. Atherosclerosis along the aortic surface of the valve calcifies subsequent to aortic valvular osteoblast differentiation to create a calcific area. In time, the calcific area can grow to between 1.0 cm and 1.7 cm in diameter. Calcific stenosis occurs when enough calcium has accumulated along the surface of the aortic valve leaflets to impede the flow of blood out of the left ventricle. If a patient has a calcific aortic valve, the current TAVI procedure and corresponding replacement valves can cause further complications during implantation. Since the TAVI replacement valves currently on the market push the aortic valves upward and outward, such that the native aortic valve forms a coaxial layer between the aorta and replacement valve, calcium build up can increase the radial pressure applied to the AV node, Bundle of His, and Purkinje fibers.

Heavily calcified aortic valves cannot be dilated evenly during valvuloplasty due to the uneven size and distribution of calcium deposits on calcific aortic valves. Uneven dilation of the native aortic valve alone can result in dislodgement of the TAVI replacement valve or paravalvular leaks. Coupled with unevenly shaped and distributed calcium deposits, uneven dilation can cause aortic dissection with crashing of the Bundle of His or left Bundle due to the radial pressure of the TAVI replacement valve pushing calcium deposits on the native aortic valve into sensitive areas of the cardiac conductive system. Resulting cardiac conditions may include Left Bundle Branch Block (LBBB), Right Bundle Branch Block (RBBB), and Atrioventricular Block (AVB). Patients who undergo the TAVI procedure and develop arrhythmias or one of the aforementioned blocks often require permanent pacemakers to maintain consistent and regular heart rates. By relieving the restriction of blood flow caused by aortic stenosis, the current TAVI method and replacement valves may cause other critical cardiac issues for patients without any prior history of arrhythmias or conductive conditions.

The biggest consequence of current TAVI replacement valve issues is the additional medical procedures and equipment needed to counteract conduction problems. In nearly 70% of patients currently receiving a TAVI replacement valve, an artificial pacemaker must be inserted to rectify conduction issues caused largely by calcium deposits on the native aortic valve crushing the cardiac conductive system during the implantation of the TAVI replacement valve.

The inventions and embodiments described herein solve current issues with TAVI procedures by largely removing calcium deposits from the aortic valve.

SUMMARY OF INVENTION

The present invention solves the problem of improper implantation of current TAVI replacement valves by disclosing a totally percutaneous method and device for removing a significant portion of calcific deposits on a native aortic valve to lower conductive interference, while preserving enough calcific deposits around the circumference of the native aortic valve to aid in the stabilization of the TAVI replacement once implanted. Various embodiments of the present invention are disclosed.

In an embodiment, a totally percutaneous device for removing calcium deposits from an aortic valve comprises a punch system including a collapsible male element positioned coaxially around at a distal end of a primary tube and spaced apart from a collapsible female element positioned coaxially around the primary tube proximal to the male element; a collapsible filter umbrella positioned coaxially around the primary tube proximal to the female element; a first removable cover positioned coaxially around the primary tube for covering and uncovering the collapsible male element such that the male element is collapsed when covered by the first removable cover; a second removable cover positioned coaxially around the primary tube for covering and uncovering the collapsible female element such that the female element is collapsed when covered by the second removable cover; a third removable cover positioned coaxially around the primary tube for covering and uncovering the collapsible filter umbrella such that the filter umbrella is collapsed when covered by the third removable cover; and a control system positioned at the proximal end of the primary tube and controlling the first removable cover, second removable cover, and third removable cover to cover and uncover the male element, the female element, and the filter umbrella, respectively, wherein the control system includes a punch control driver actuating the uncollapsed male element and the uncollapsed female element to advance and retreat relative to one another within the aortic valve. The male element has teeth positioned along a circumferential edge of the proximal end, and the female element has groves positioned along a circumferential edge of the distal end positioned to accept the teeth of the male element. The device may further comprise a motor assembly attached to the male element, wherein the motor assembly includes a high speed motor attached to the male element via a cable and an operator control element is attached to the high speed motor, and wherein the operator control element is configured to active or deactivate the high speed motor, which when activated rotatably closes the male element against the female element.

In another embodiment, a totally percutaneous device for removing calcium deposits from an aortic valve comprises a collapsible filter umbrella positioned coaxially around at a distal end of a primary tube; a punch system including a collapsible female element positioned coaxially around the primary tube proximal to the filter umbrella and spaced apart from a collapsible male element positioned coaxially around the primary tube proximal to the female element; a first removable cover positioned coaxially around the primary tube for covering and uncovering the collapsible male element such that the male element is collapsed when covered by the first removable cover; a second removable cover positioned coaxially around the primary tube for covering and uncovering the collapsible female element such that the female element is collapsed when covered by the second removable cover; a third removable cover positioned coaxially around the primary tube for covering and uncovering the collapsible filter umbrella such that the filter umbrella is collapsed when covered by the third removable cover; and a control system positioned at the proximal end of the primary tube and controlling the first removable cover, second removable cover, and third removable cover to cover and uncover the male element, the female element, and the filter umbrella, respectively, wherein the control system includes a punch control driver actuating the uncollapsed male element and the uncollapsed female element to advance and retreat relative to one another within the aortic valve. The male element may have teeth positioned along a circumferential edge of the proximal end and the female element has groves positioned along a circumferential edge of the distal end positioned to accept the teeth of the male element. The device may further comprise a motor assembly attached to the male element, wherein the motor assembly includes a high speed motor attached to the male element via a cable and an operator control element is attached to the high speed motor, and wherein the operator control element is configured to active or deactivate the high speed motor, which when activated rotatably closes the male element against the female element.

In another embodiment, a method of a totally percutaneous aortic punch for removing calcium deposits from an aortic valve comprises inserting a device through an aortic valve, wherein the device has a collapsible filter umbrella for catching debris from operation of the device and a collapsible punch system for perforating the aortic valve; positioning the punch system within the native aortic valve, wherein a male element and a female element of the punch system are collapsed to avoid inadvertent damage to surrounding tissue, and wherein the male element and female element are on positioned on opposite sides of native aortic valve; positioning the collapsed filter umbrella in an aorta downstream of blood flow through the aortic valve, such that the filter umbrella allows blood to pass beyond the aorta and catches debris; uncompressing the collapsed male element, female element, and filter umbrella; perforating the aortic valve to remove calcium deposits from the aortic valve; and leaving a ring of calcium deposits along the circumference of the native aortic valve. The device may be inserted through the native aortic valve transapically. The device may be inserted through the native aortic valve transfemorally or transaortically. The device may be implemented by one of the other embodiments disclosed above.

In another embodiment, a collapsible punch system for totally percutaneous removal of calcium deposits from an aortic valve comprises a male element having a center ring and a plurality of symmetrical spokes increasing in width toward a common circumference, the male element being deformable to a closed conical shape in which the spokes form a continuous ring at the circumference, wherein the spokes are collapsible to a cylinder shape when compressed and return the conical shape when uncompressed; a female element having a center ring and a plurality of symmetrical spokes increasing in width toward a common circumference, the female element being deformable to a closed conical shape in which the spokes form a continuous ring at the circumference, wherein the spokes are collapsible to a cylinder shape when compressed and return the conical shape when uncompressed; and a punch control element configured to move the collapsible male element in relation to the collapsible female element when the male element and the female element are uncompressed, wherein the female element receives the male element. The ends of the spokes may form a cutting edge at the circumference of the conical shape. The cutting edge may form a uniform circle about a plane or a plurality of teeth in one of a sine wave, square, triangle, or sawtooth pattern. The male element and the female element may be formed of nitinol. The male element and the female element may be formed of a shape memory alloy.

Other embodiments of these processes and devices are described herein. These embodiments are not exclusive of the only possible embodiments. A further understanding of the structural, functional, and advantageous aspects of the disclosure can be realized by reference to the following detailed description and drawings.

BRIEF DESCRIPTION OF DRAWINGS

Figures accompanying the specification show and describe the inventions, as follows:

FIG. 17A shows an exemplary totally percutaneous collapsible aortic punch device in accordance with the present invention;

FIG. 17B shows an exploded view of a second cover in the totally percutaneous collapsible aortic punch device in accordance with the present invention;

FIG. 17C shows an exploded view of a third cover in the totally percutaneous collapsible aortic punch device in accordance with the present invention;

FIG. 17D shows an exploded view of a spindle in the totally percutaneous collapsible aortic punch device in accordance with the present invention;

FIG. 18A shows an exemplary totally percutaneous collapsible aortic punch device in accordance with the present invention;

FIG. 18B shows an exploded view of the third cover in the totally percutaneous collapsible aortic punch device in accordance with the present invention;

FIG. 18C shows an exploded view of a spindle in the totally percutaneous collapsible aortic punch device in accordance with the present invention;

FIG. 18D shows an exploded view of the second cover in the totally percutaneous collapsible aortic punch device in accordance with the present invention;

FIG. 18E shows an exploded view of a spindle in the totally percutaneous collapsible aortic punch device in accordance with the present invention;

FIG. 18F shows a totally percutaneous collapsible punch in accordance with the present invention;

FIG. 20A shows an exemplary totally percutaneous collapsible aortic punch device in accordance with the present invention;

FIG. 20B shows an exploded view of a closed totally percutaneous collapsible punch in accordance with the present invention;

FIG. 20C shows an exploded view of a spindle in the totally percutaneous collapsible aortic punch device in accordance with the present invention;

FIG. 22A shows an exemplary totally percutaneous collapsible aortic punch device in accordance with the present invention;

FIG. 22B shows an exploded view of an open totally percutaneous collapsible punch operatic in an aortic valve in accordance with the present invention;

FIG. 22C shows an exploded view of a spindle in the totally percutaneous collapsible aortic punch device in accordance with the present invention;

FIG. 22D shows an exploded view of a spindle in the totally percutaneous collapsible aortic punch device in accordance with the present invention;

Throughout the drawings, it should be noted that like reference numbers are used to depict the same or similar elements, features, and structures.

DETAILED DESCRIPTION OF INVENTION

Various embodiments and aspects of the disclosure are described with reference to details discussed below. The following descriptions and referenced drawings are illustrative of the disclosure and are not to be construed as limiting the disclosure. The drawings are not necessarily to scale. Numerous specific details are described to provide a thorough understanding of various embodiments of the present disclosure. However, in certain instances, well-known or conventional details are not described in order to provide a concise discussion of embodiments of the present disclosure.

As used herein, spatial and relative terms such as "proximal" and "distal" are relative to a user of the methods or devices described herein, unless otherwise stated. For example, a distal end of a tube is the end farthest from a user, whereas a proximal end of the same tube is the end closest to the user.

Figure 6A:
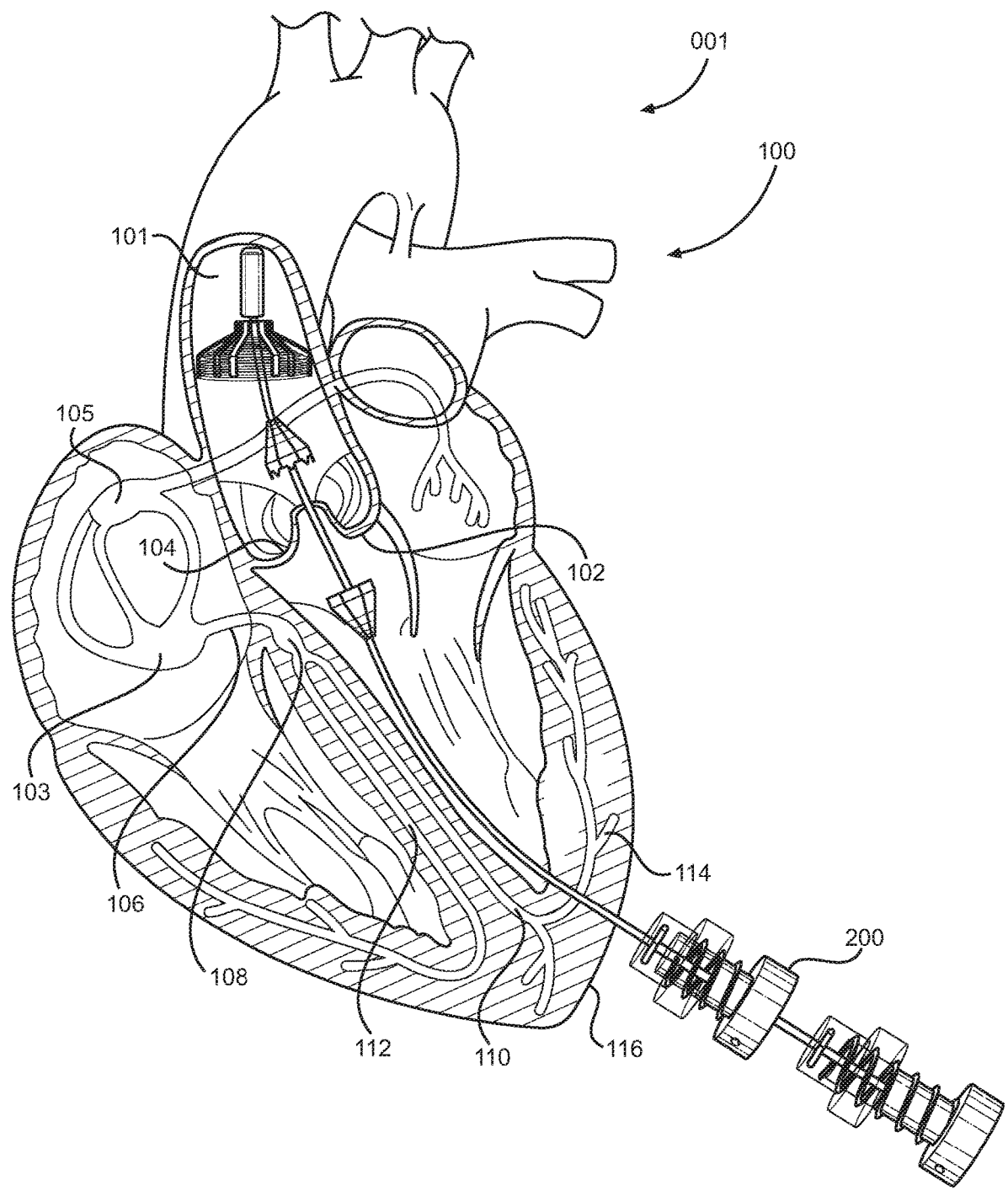
FIG. 6A shows a representative procedure using a device inserted apically up through the left ventricle and into the aorta in accordance with the present invention.
Figure 6B:
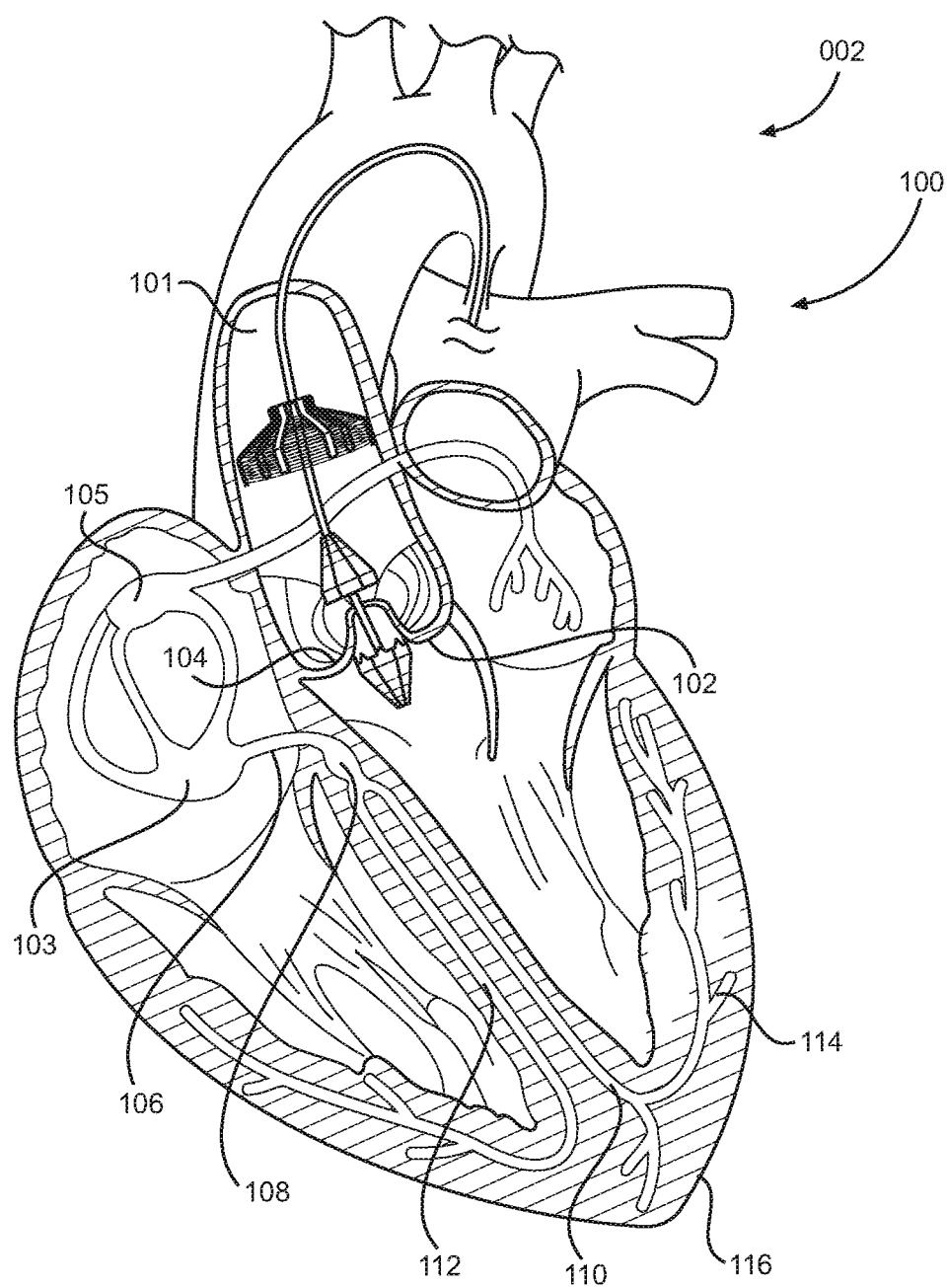
FIG. 6B shows a representative procedure using a device inserted transfemorally through the femoral artery, up through the aorta and down into the aortic valve in accordance with the present invention.
Figure 6C:
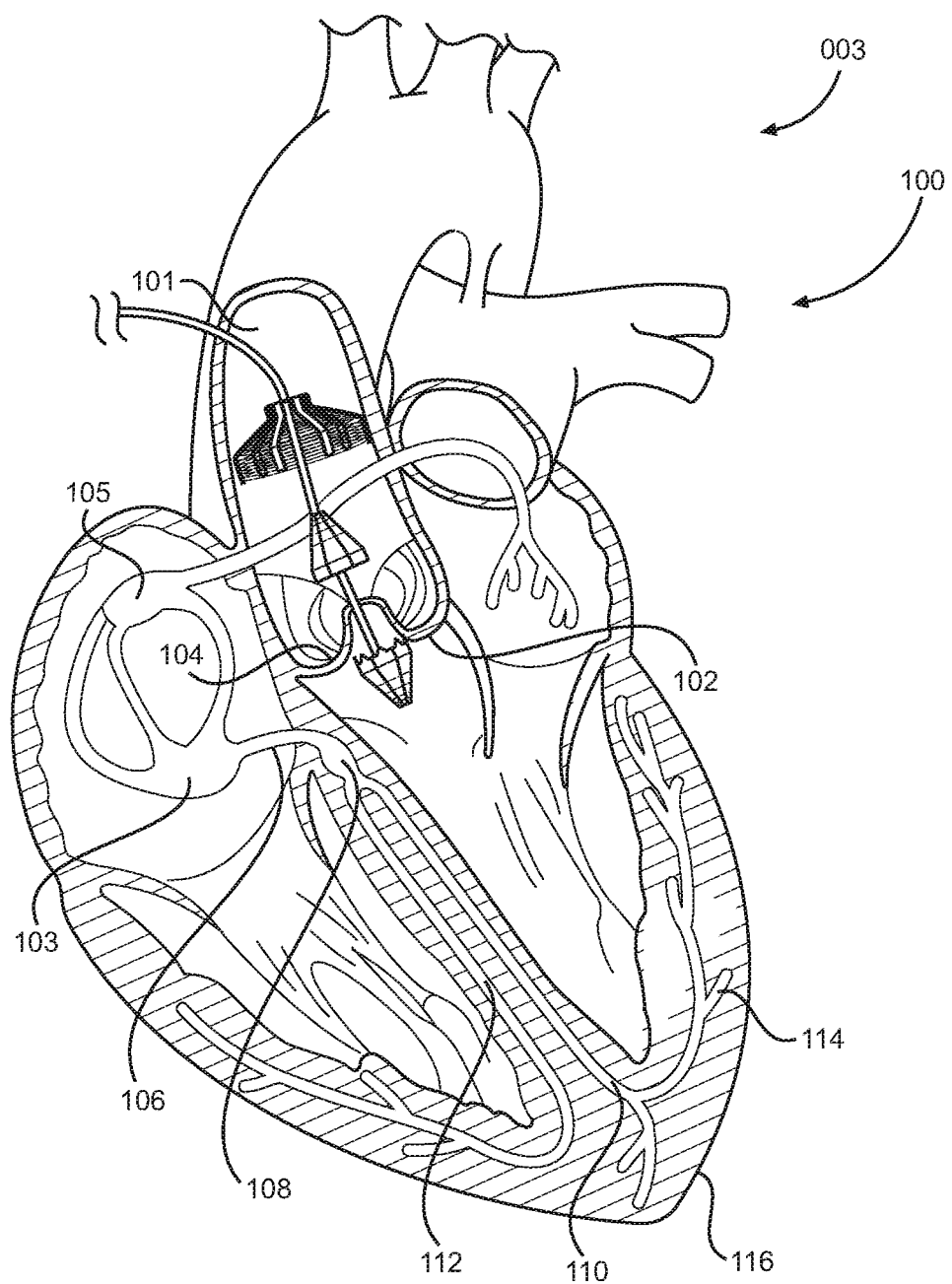
FIG. 6C shows a representative procedure using a device inserted transaortically through the aorta artery and down into the aortic valve in accordance with the present invention.
Figure 7A:
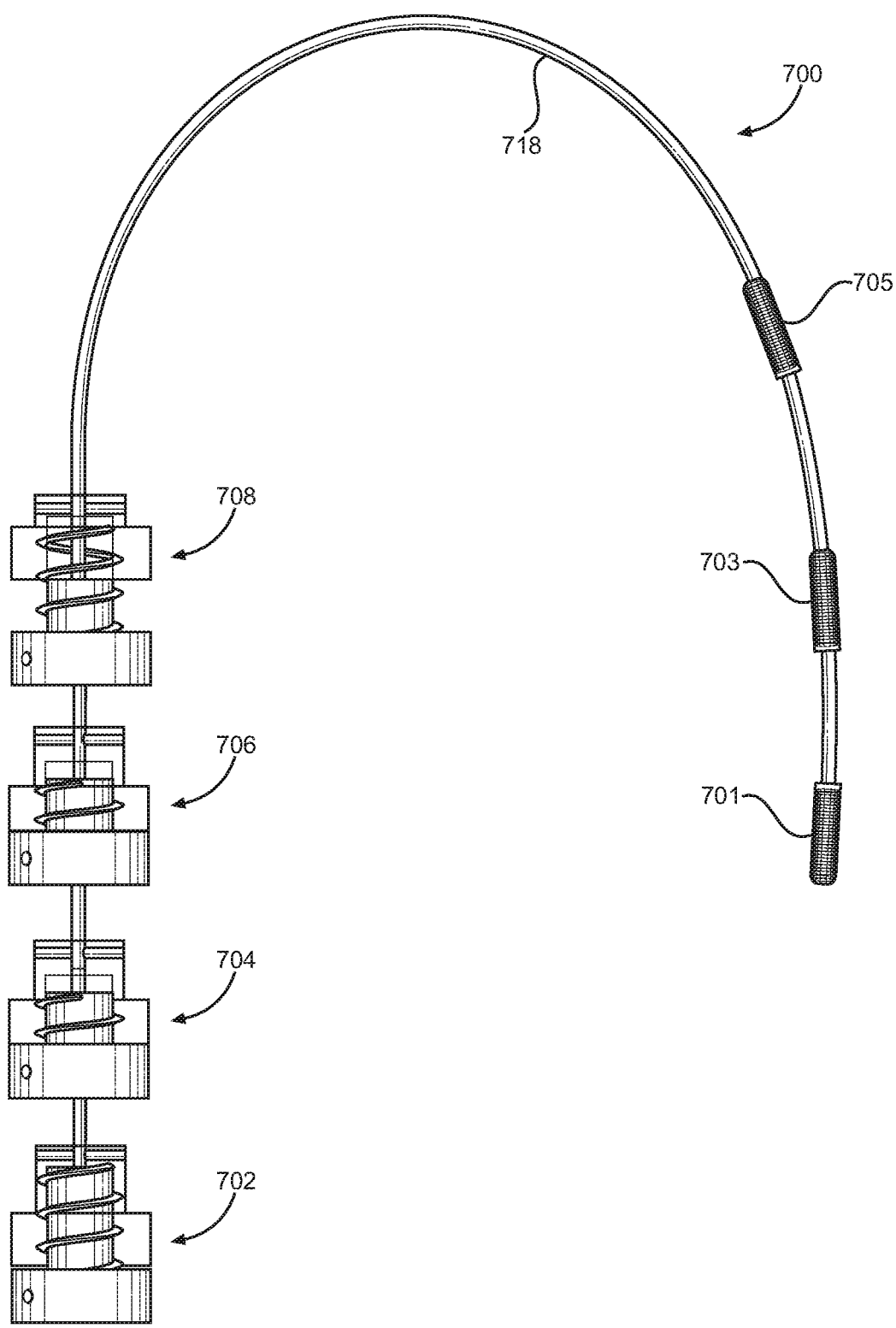
FIG. 7A shows an embodiment of a totally percutaneous collapsible aortic punch device in accordance with the present invention.
Figure 7B:
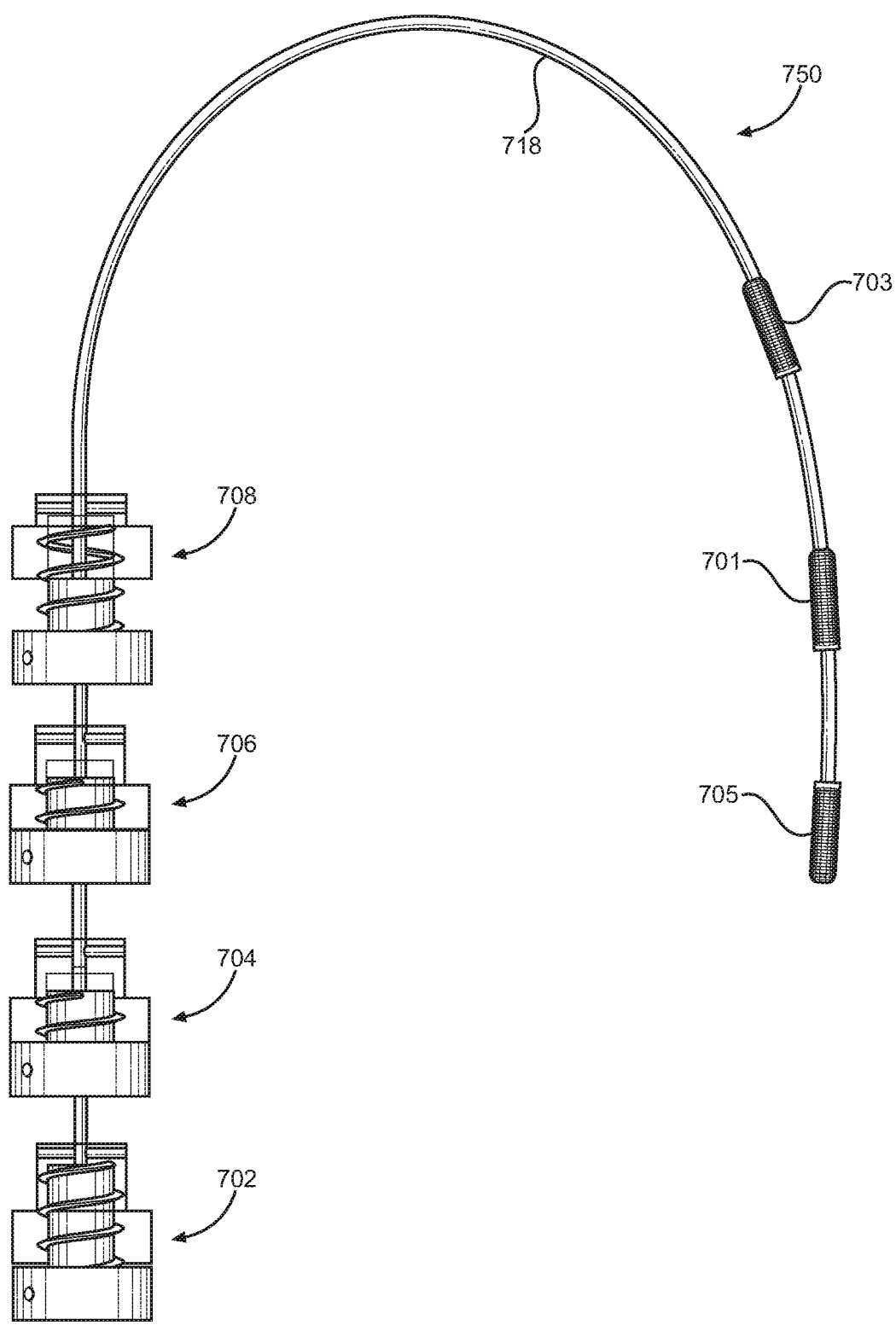
FIG. 7B shows another embodiment of a totally percutaneous collapsible aortic punch device in accordance with the present invention.

With reference to FIGS. 7A, 7B, 8, and 9, a preferred embodiment for the method for a totally percutaneous collapsible aortic punch for use in transcather aortic valve implantation. For transfemoral and transaortic insertion of the collapsible punch system, the method includes inserting a device 700 through a native aortic valve 526, wherein the device includes, at the distal end, a male cover 701 for housing a male element 711 of the collapsible punch 902 in a collapsed state, female cover 703 for housing a female element 713 of the collapsible punch 902 in a collapsed state proximal from the male cover 703, and cover 705 for housing filter umbrella 715 in a collapsed state proximal from the female cover 703. For transapical insertion, FIG. 7B illustrates a device 750 that is substantially the same as device 700 in FIG. 7A, except that cover 705 for housing filter umbrella 713 is located at the distal end after cover 701 for housing male element 711. For reference, FIG. 6A shows an embodiment of the device 750 inserted transapically through an apex 116 of a heart 001, FIG. 6B shows the device 700 inserted transfemorally, and FIG. 6C shows the device 700 inserted transaortically.

Figure 8:
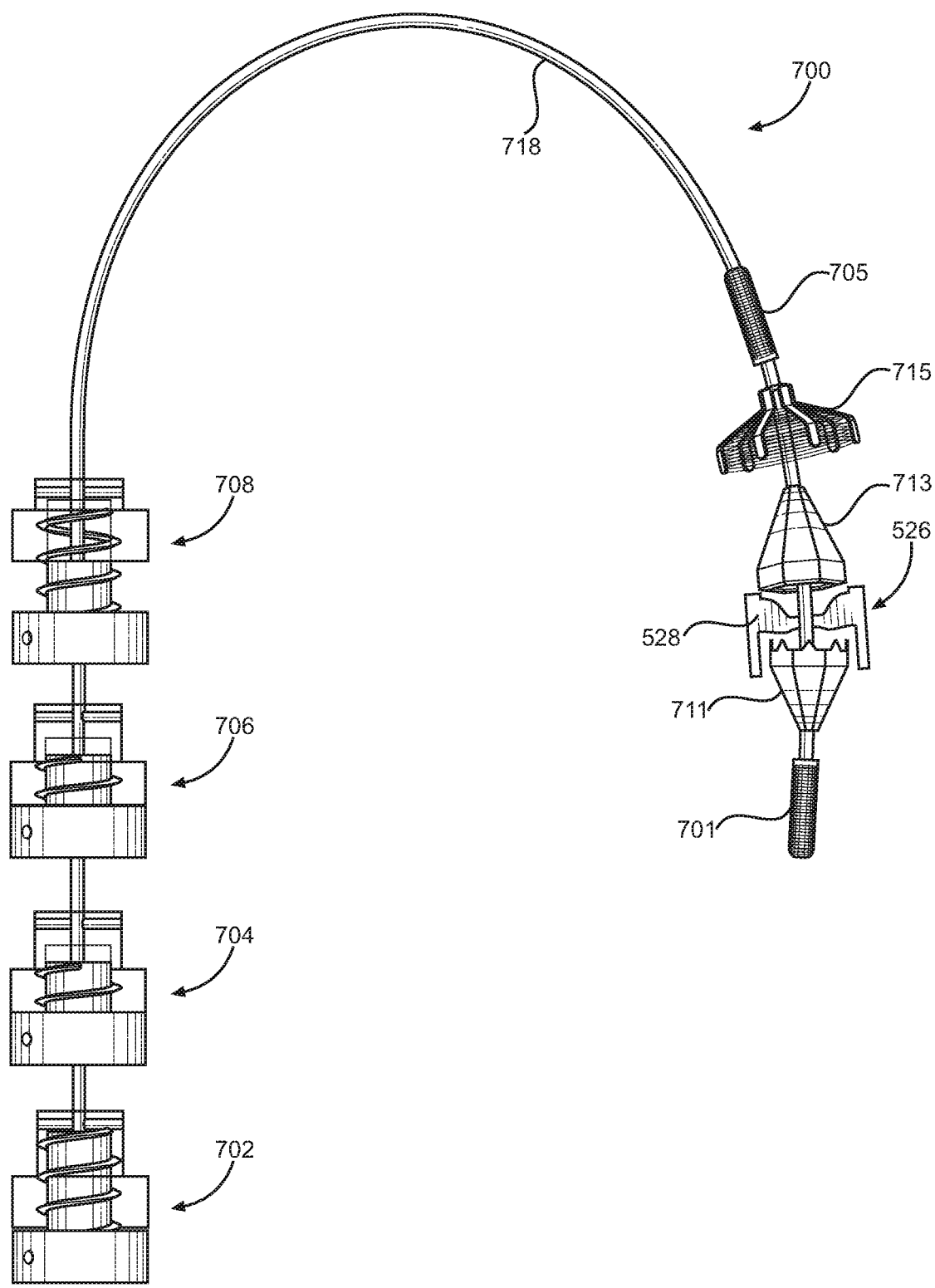
FIG. 8 shows an uncollapsed totally percutaneous collapsible aortic punch device in accordance with the present invention.
Figure 9:
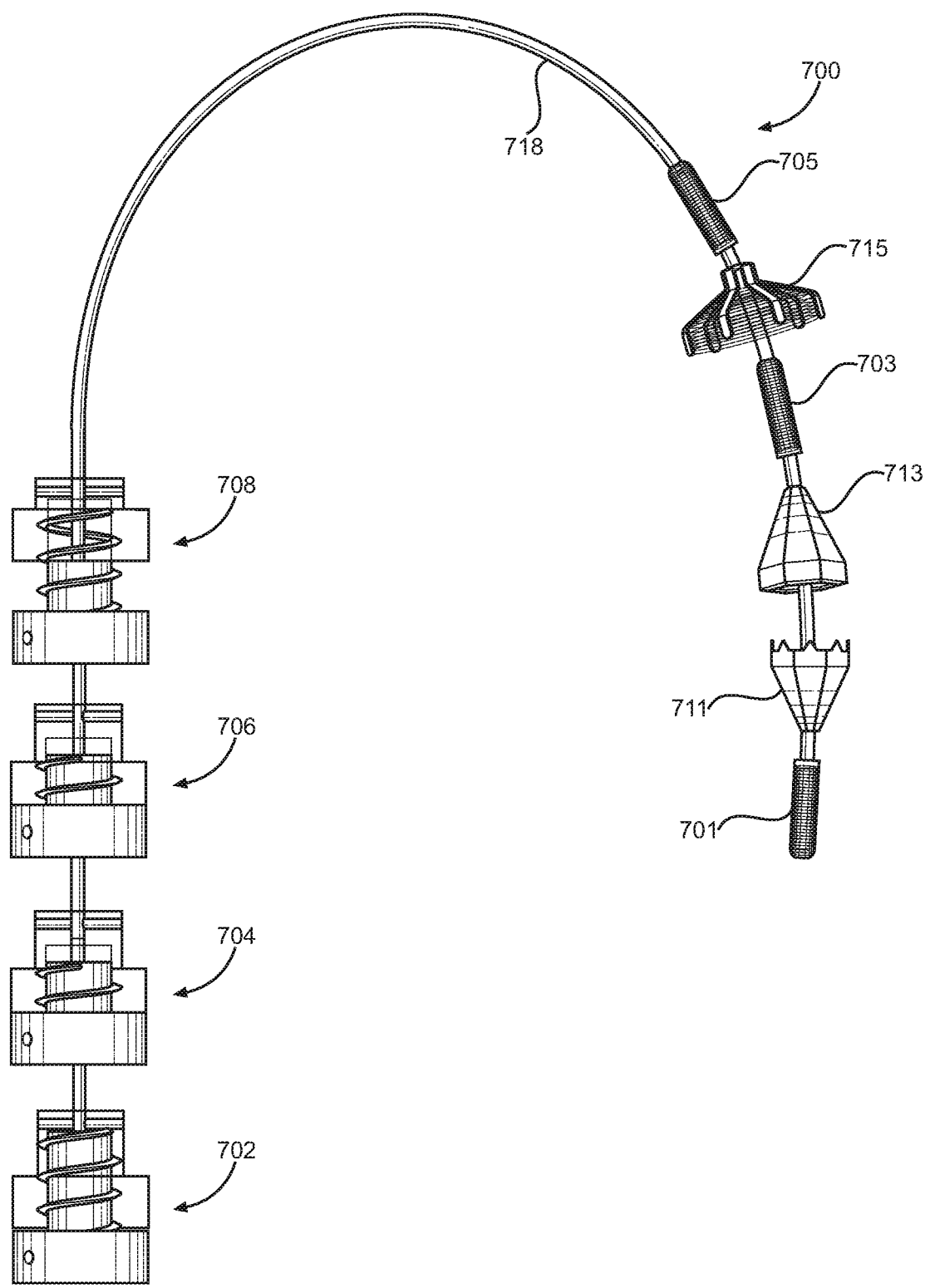
FIG. 9 shows an uncollapsed totally percutaneous collapsible aortic punch device in accordance with the present invention.

A next step is positioning the punch 902 within the native aortic valve 526, wherein covers 701, 703, and 705 are retracted to decompress, respectively, male element 711, female element 713, and filter umbrella 715, as shown in FIG. 8. The male element 711, female element 713, and filter umbrella 715 are compressed during insertion and positioning of the punch 902 in the native aortic valve 526 to minimize the detachment of calcium deposits from the aortic leaflets 528 in the aorta, thereby decreasing the risk of an embolism. The retraction of the covers 701, 703, and 705, is achieved through operation of reversely-threaded actuator spindles 702, 706, and 708. Spindle 702 is operated by the user to control the cover 701 that compresses the male element 711, spindle 706 is operated by the user to control the cover 703 that compresses the female element 713, and spindle 708 is operated by the user to control the cover 705 that compresses the filter umbrella 715. Meanwhile, reversely-threaded actuator spindle 704 controls the distance between the male element 711 and female element 713 of the punch 902, and thus is operated by the user to control the operation of the punch 902.

With reference to FIGS. 20A, 20B, and 20C, a next step includes closing the un-collapsed punch 902 over the aortic valve leaflets 528 so that the male element 711 applies force along cutting edge teeth 711a to a superior surface the aortic valve leaflets 528 and the female element 713 applies force along cutting edge 713a to an inferior surface of the aortic valve leaflets 528. FIG. 20B illustrates the punch 902 in a closed formation in the native aortic valve 526. Closing of the punch 902 is achieved by operation of spindle 704 as shown in FIG. 20C.

Figure 5:
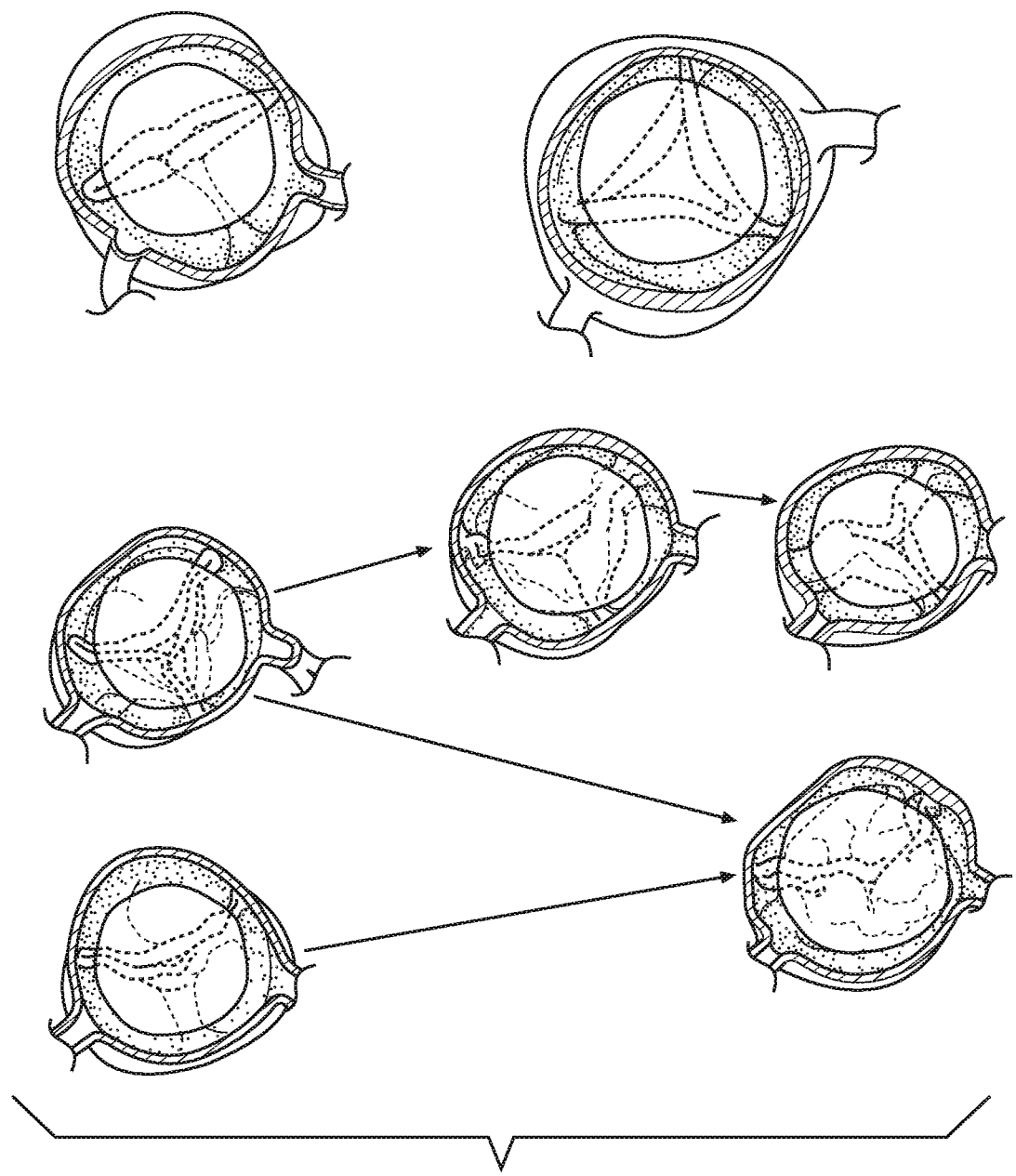
FIG. 5 shows a representative sampling of the different stenotic aortic valves that have been perforated by the improved method and disclosed devices.

Another step includes perforating the native aortic valve 526 via the punch 902 to remove calcium deposits from the native aortic valve. FIG. 5 shows representations of the perforation of the native aortic valve 526 once the device 700 is removed. The perforation of the native aortic valve 526 should leave a circumferential ring of the remaining tissue of the native aortic valve with a preferable length of 2-3 millimeters.

The final step includes leaving a ring of calcium deposits 534, as shown in FIG. 5, along the circumference of the native aortic valve 526. A semi-rigid ring composed of the remaining aortic valve is useful in stabilizing any TAVI replacement valve during and after implantation. Additionally, less radial pressure is ultimately placed on the heart conduction system as the majority of the calcium deposits are removed from the native aortic valve that would otherwise be folded upward between a replacement valve and aorta. Further, the chance of paravalvular leaks is reduced, as the shortened aortic leaflets make proper insertion of replacement valves easier and more successful.

Figure 1:
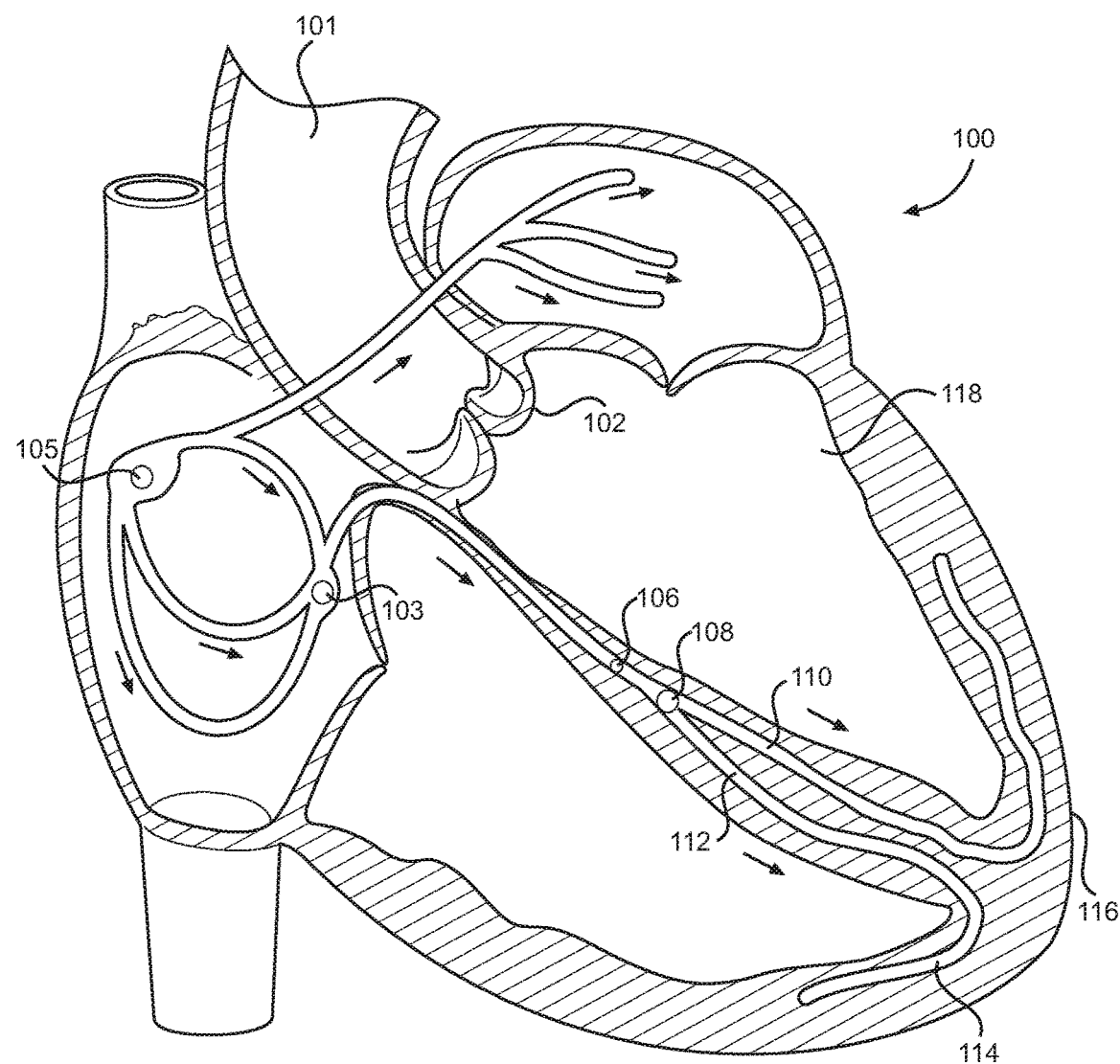
FIG. 1 shows a representation of the cardiac conduction system.
Figures 2A, 2B, 2C:
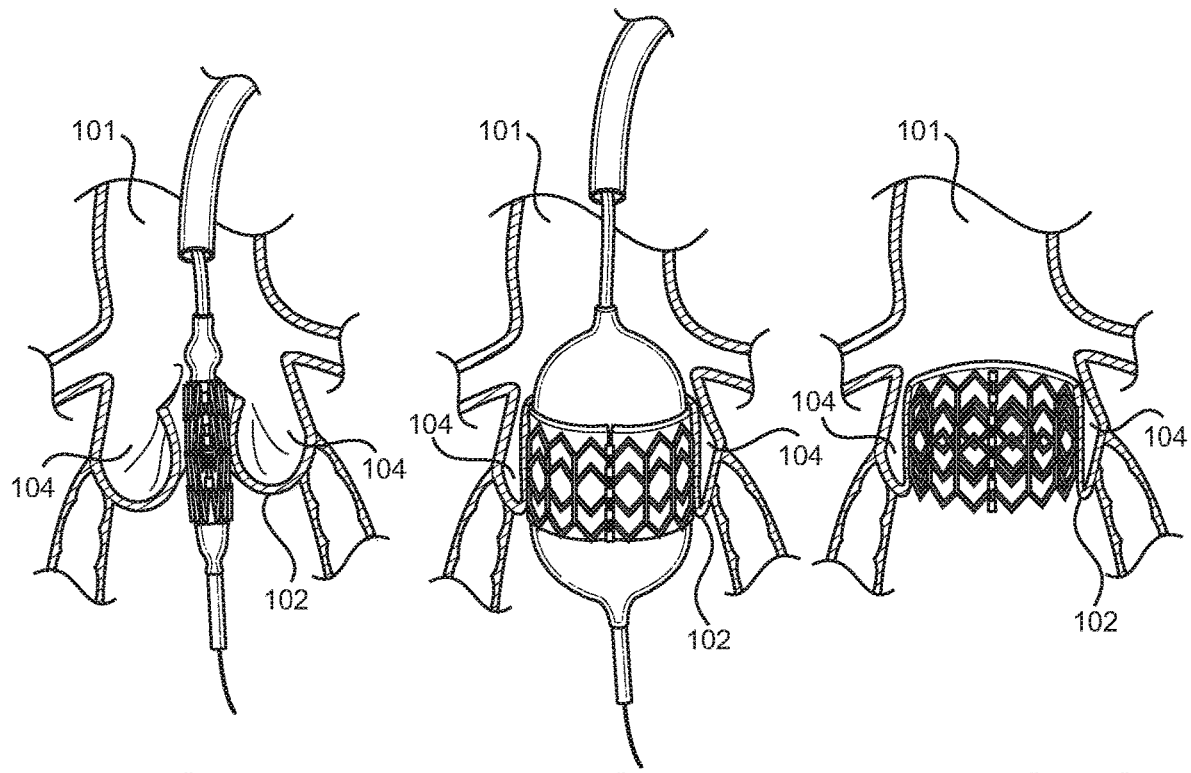
FIG. 2A shows a traditional implantation of TAVI replacement valve, namely a catheter with a collapsed replacement valve attached coaxially around an outside surface positioned within an aortic valve.
FIG. 2B shows a traditional implantation of TAVI replacement valve, namely expansion of the replacement valve within the aortic valve via a balloon catheter.
FIG. 2C shows a traditional implantation of TAVI replacement valve, namely the TAVI replacement valve fully expanded and implanted within a native aortic valve.
Figures 3A, 3B, 3C:
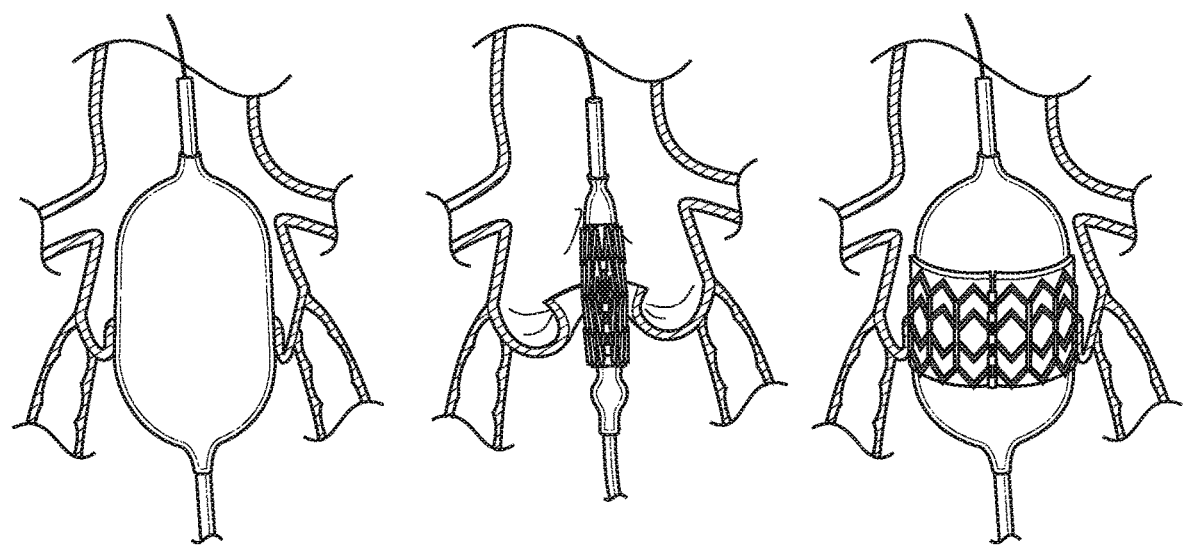
FIG. 3A shows expansion of a balloon catheter inside an aortic valve perforated by the improved process to demonstrate the reduced radial pressure due to shorter aortic leaflets.
FIG. 3B shows an improved implantation of TAVI replacement valve, namely a catheter with a collapsed replacement valve attached coaxially around an outside surface positioned within a perforated aortic valve.
FIG. 3C shows an improved implantation of TAVI replacement valve, namely expansion of the replacement valve within the aortic valve via a balloon catheter.
Figure 4:
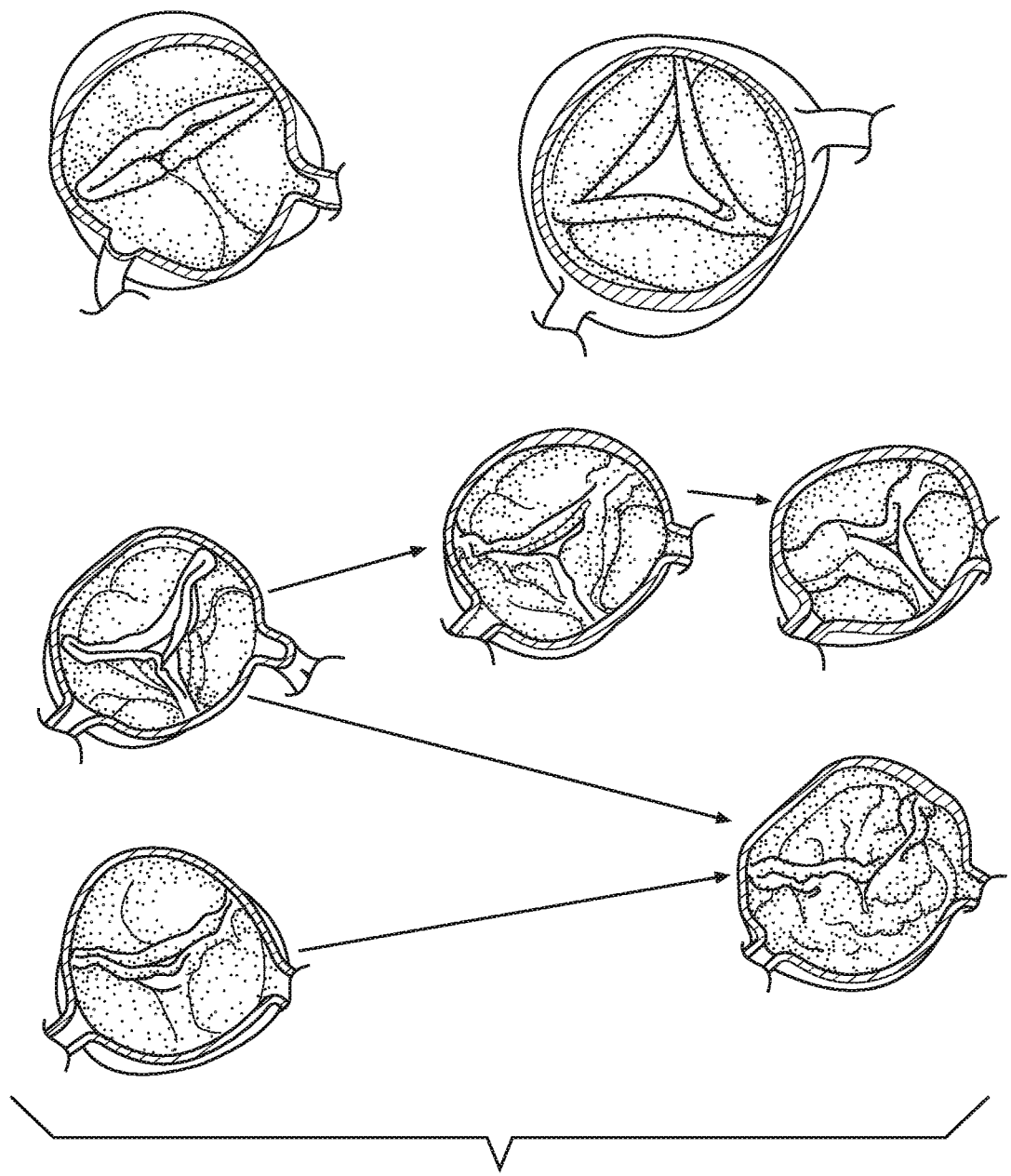
FIG. 4 shows a representative sampling of different stenotic aortic valves.

FIGS. 3A-3C show the implantation of a TAVI replacement valve after using the process described herein. FIG. 3A shows insertion of a balloon catheter and replacement valve into the perforated aortic valve. FIG. 3B shows the inflation of the catheter and resulting expansion of the replacement valve. FIG. 3C shows the replacement valve implanted over the perforated aortic valve, with the remaining circumferential ring of the aortic valve, with some calcification, providing a structural support for the replacement valve. FIG. 5 shows the same stenotic valves shown in FIG. 4 after the application of the described process for removing calcium deposits from aortic valves.

The male element 711 and female element 713 of the collapsible punch 902 may be formed of nitinol or other shape memory alloy, or materials with similar shape memory characteristics. To form the male element 711 and female element 713, a plate of nitinol is cut into spokes. The plate can then be heated and deformed to take the shape of the male element 711 and female element 713 as demonstrated in FIGS. 10A, 10B, 11A, 11B, 12A, and 12B. Due to the elasticity of the material, these shapes are retained when the male element 711 and female element 713 are transitioned from the compressed state to the uncompressed state in which the punch 902 is revealed.

Figure 10A:
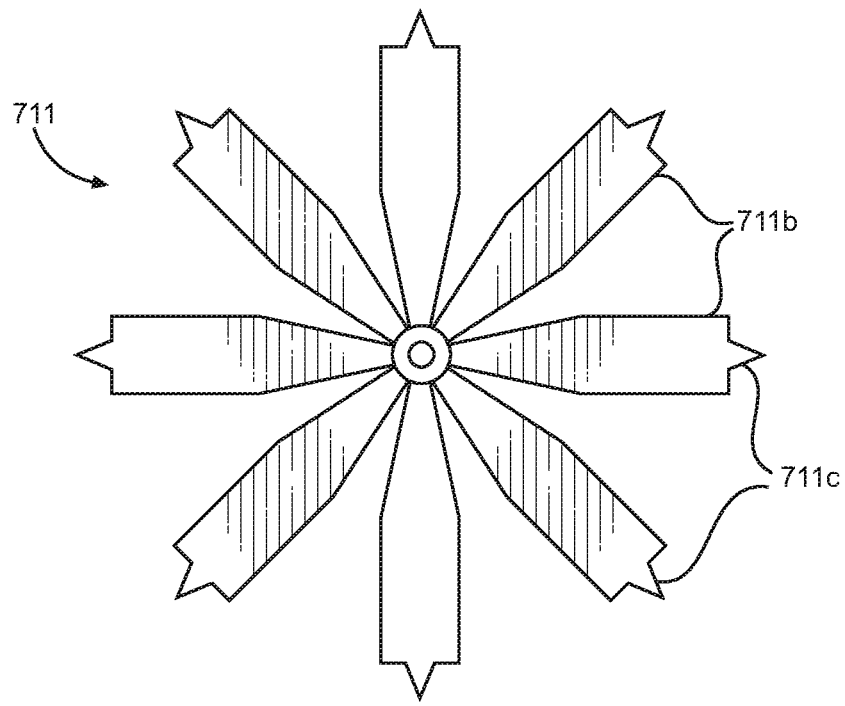
FIG. 10A shows a design of the male element of the punch device in accordance with the present invention.
Figure 10B:
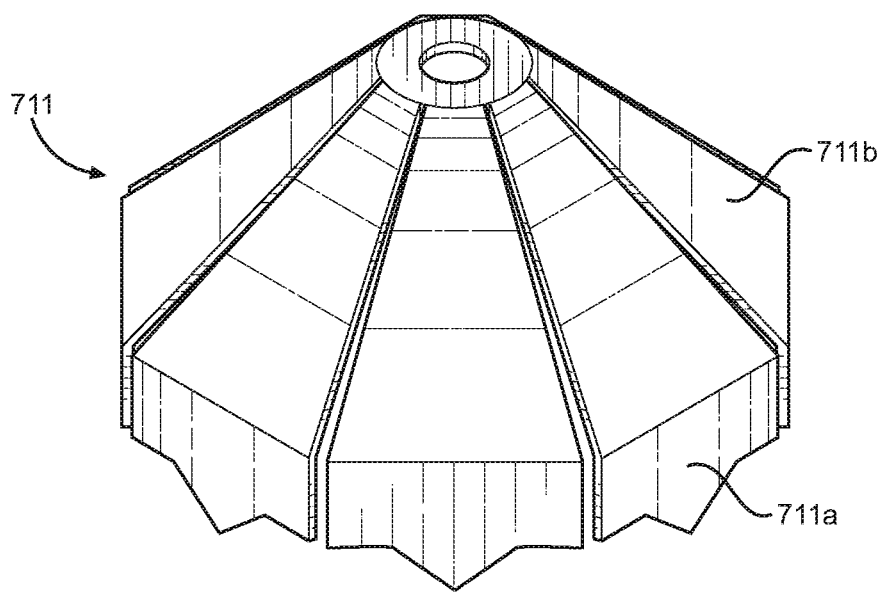
FIG. 10B shows a male element of the punch device in accordance with the present invention.

With reference to FIG. 10A, male element 711 is shown in a plan view with spokes 711b and cutting teeth 711c of the original un-deformed plate. With reference to FIG. 10B, male element 711 is shown in a perspective view of male element 711 with the spokes 711b as depicted in FIG. 10A now joined together to create the circumferential cutting edge 711a of male element 711.

Figure 11A:
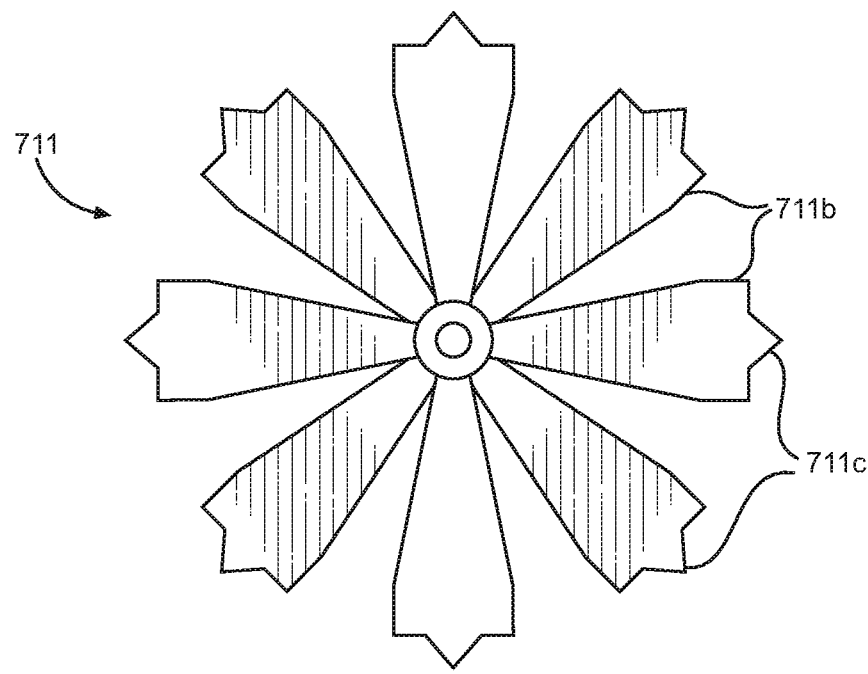
FIG. 11A shows a male element of the punch device in accordance with the present invention.
Figure 11B:
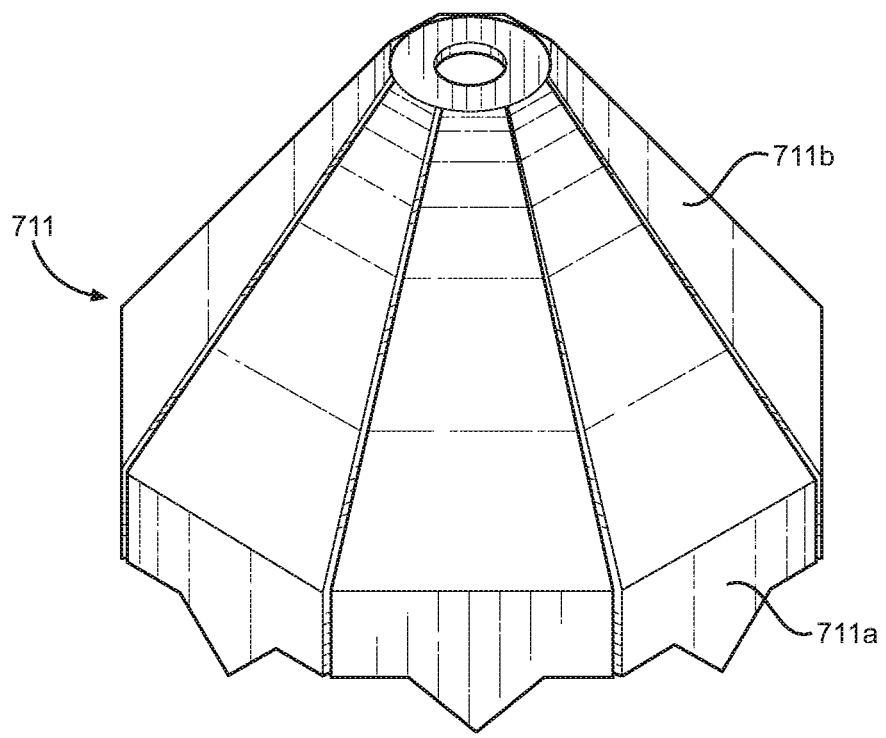
FIG. 11B shows a male element of the punch device in accordance with the present invention.

With reference to FIG. 11A, male element 711 is shown in a plan view with spokes 711b and cutting teeth 711c of the original un-deformed plate, where spokes 711b are wider than shown in FIG. 10A. With reference to FIG. 11B, male element 711 is shown in a perspective view of male element 711 with spokes 711b as depicted in FIG. 11A now joined together to create the circumferential cutting edge 711a of male element 711.

Figure 12A:
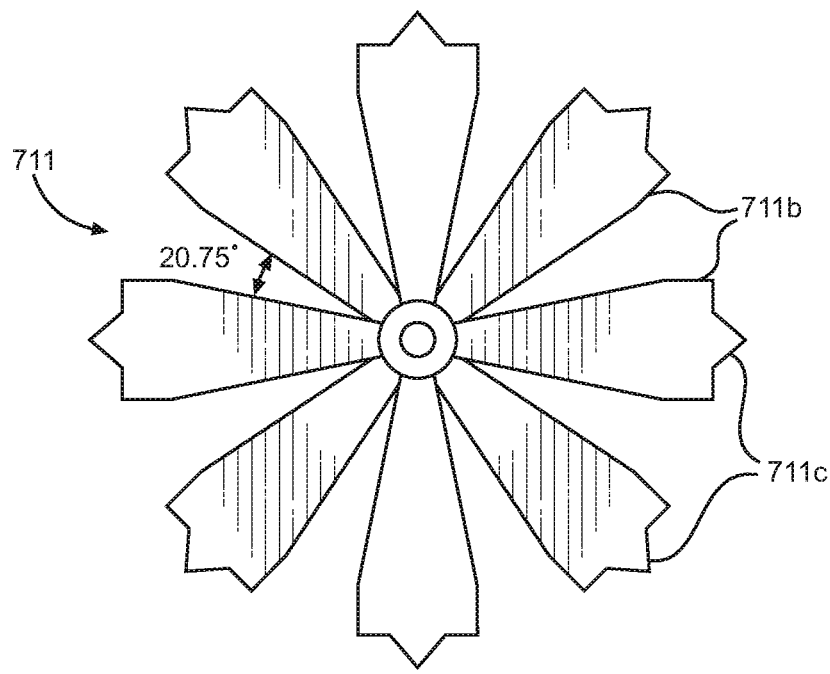
FIG. 12A shows a male element of the punch device in accordance with the present invention.
Figure 12B:
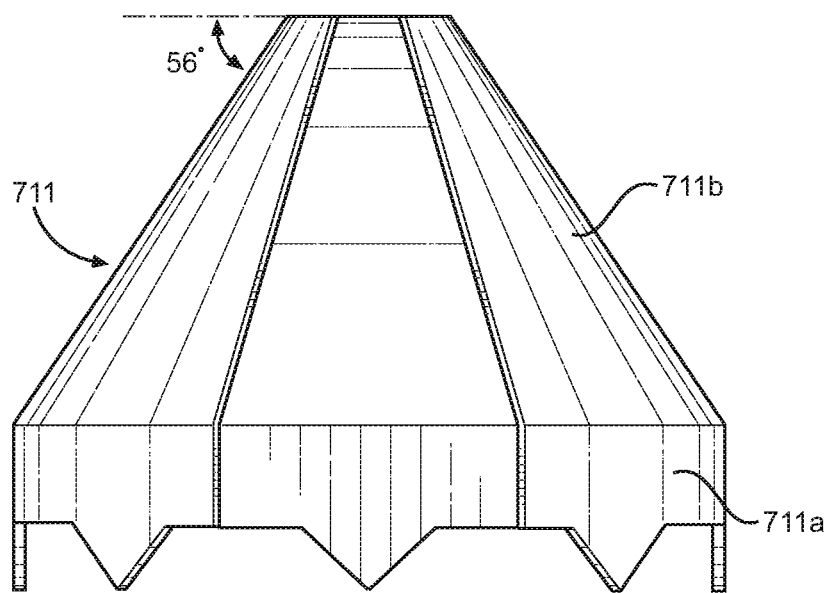
FIG. 12B shows a male element of the punch device in accordance with the present invention.

With reference to FIG. 12A, male element 711 is shown in a plan view with spokes 711b and cutting teeth 711c of the original un-deformed plate, as shown in FIG. 11A, where the angle between each spoke 711b is preferably 20.75°. With reference to FIG. 12B, male element 711 is shown in a side view with spokes 711b as depicted in FIG. 11A now joined together to create the circumferential cutting edge 711a of male element 711, where the angle between the spokes 711b and a horizontal plane is preferably 56°.

Figure 13:
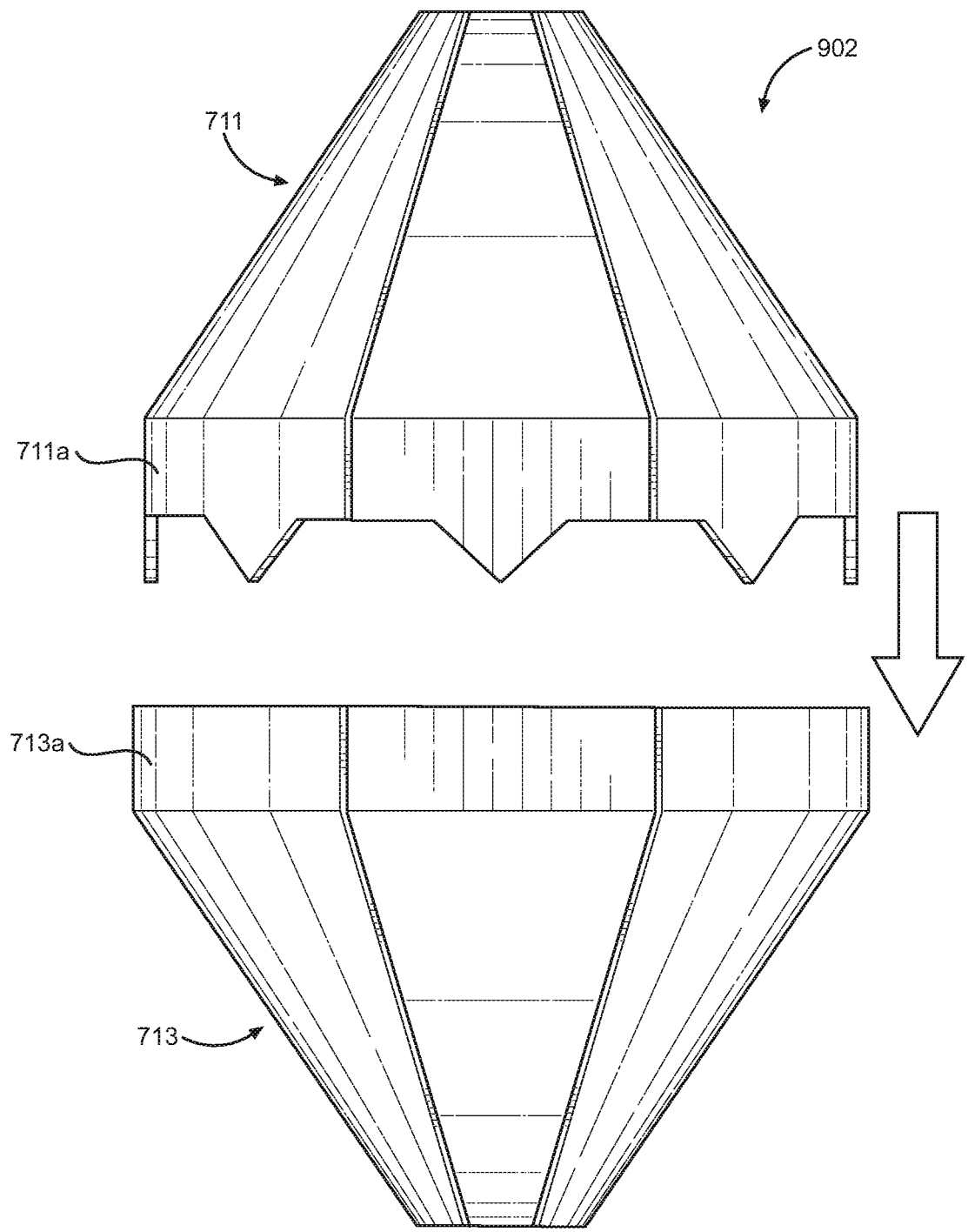
FIG. 13 shows the open male and female elements of the punch device in accordance with the present invention.
Figure 14:
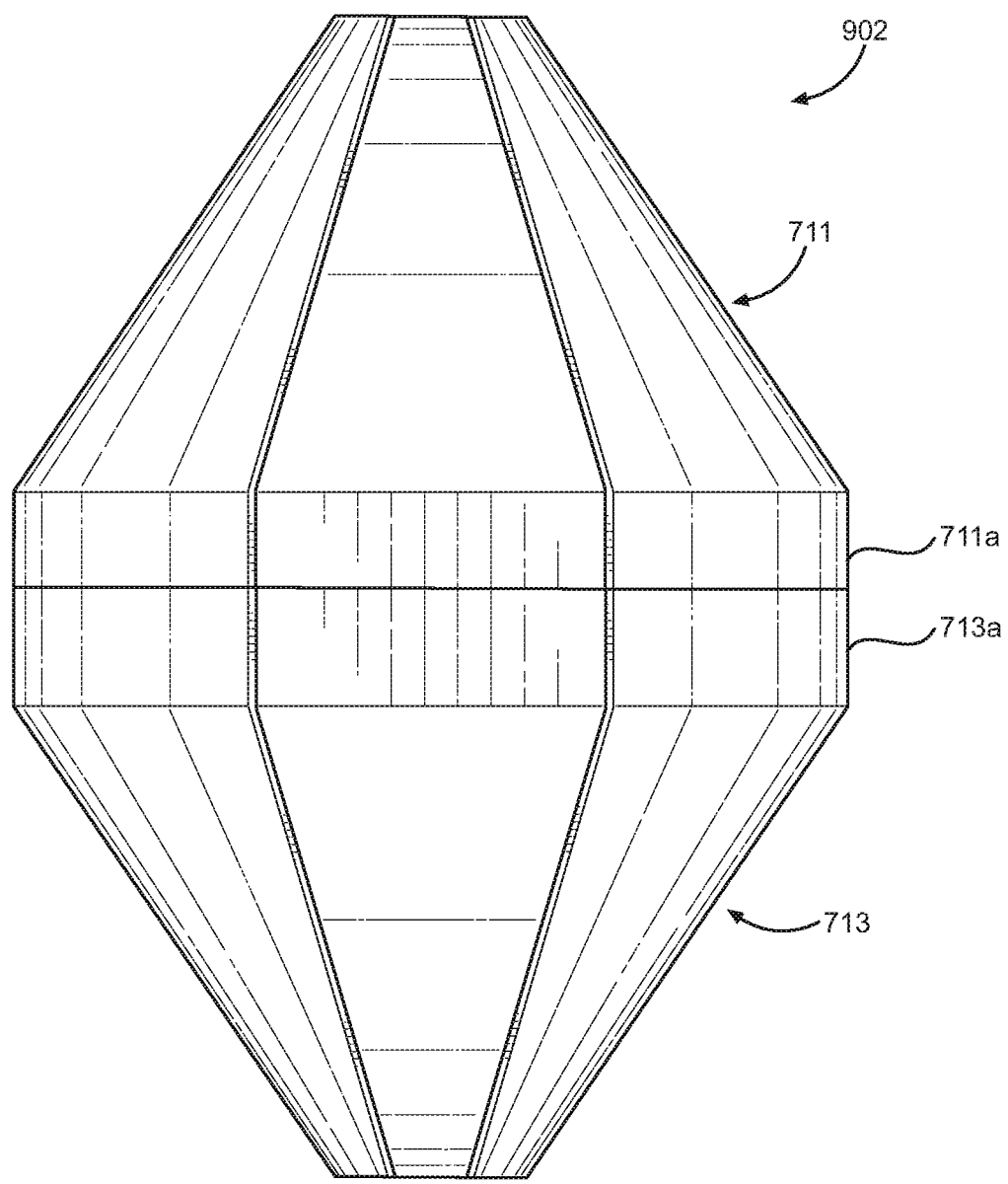
FIG. 14 shows the closed male and female elements of the punch device in accordance with the present invention.
Figure 15:
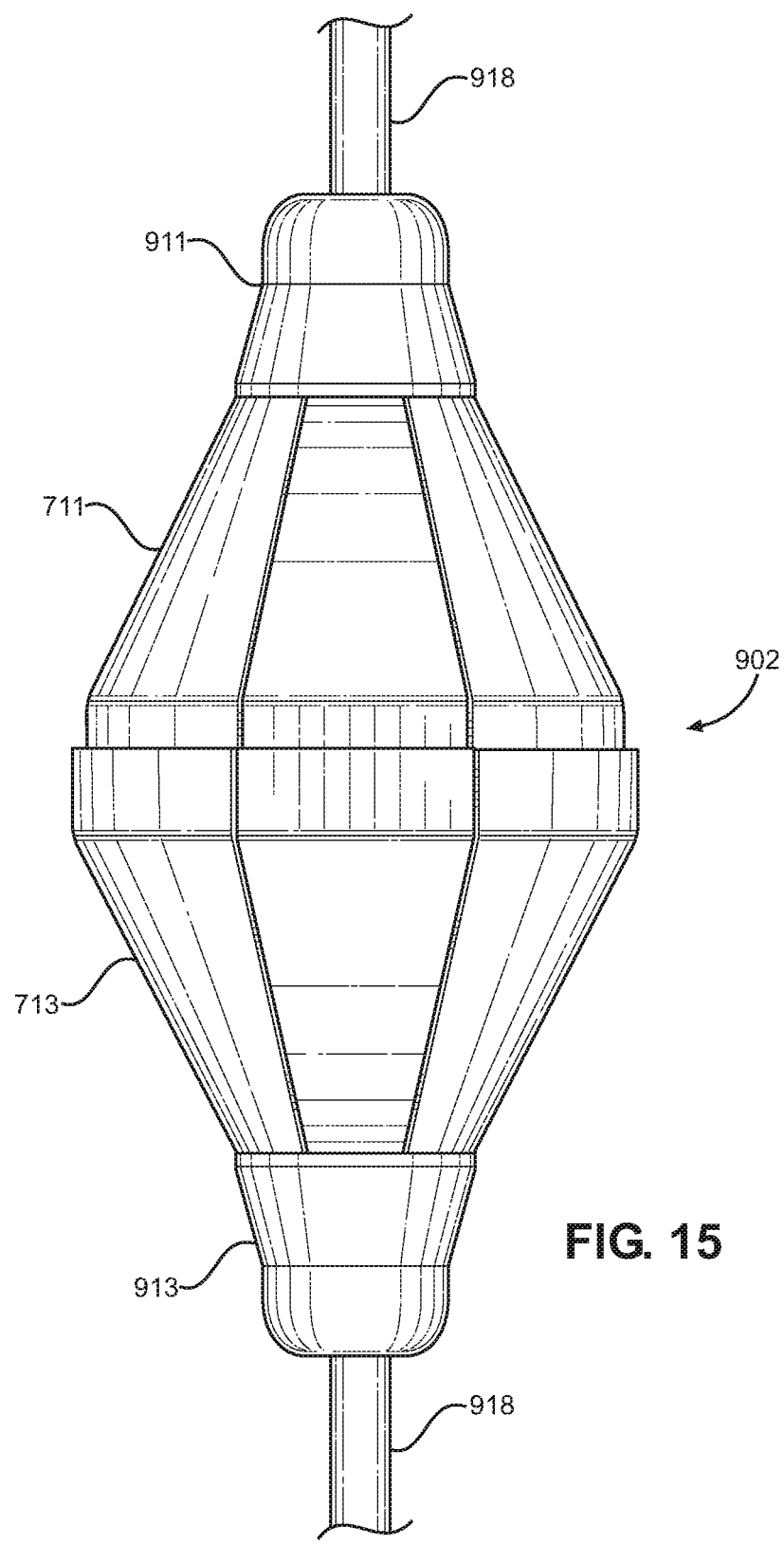
FIG. 15 shows the closed male and female elements of the punch device with caps in accordance with the present invention.
Figure 25:
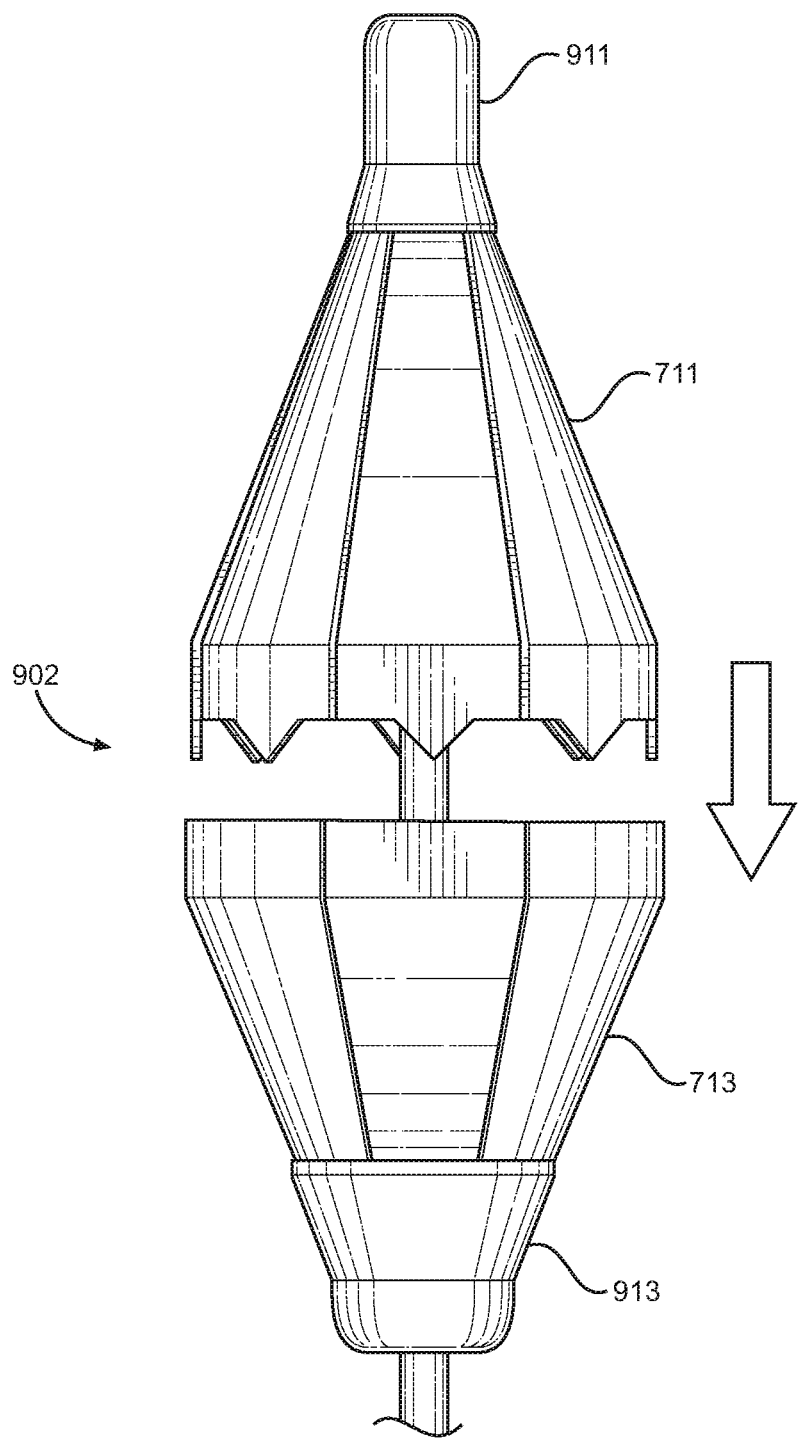
FIG. 25 shows the operation of the open male and female elements of the punch device in accordance with the present invention.

With reference to FIG. 13, the punch 902 is shown in an open state with male element 711, comprising spokes 711b and cutting edge 711a, and female element 713, comprising spokes 713b and cutting or receiving edge 713a. With reference to FIG. 14, the punch 902 is shown in a closed state with male element 711, comprising spokes 711b and cutting edge 711a, and female element 713, comprising spokes 713b and cutting or receiving edge 713a. With reference to FIG. 25, the punch 902 is open and the male element 711 is ready to be received by the female element 713, and caps 911 and 913 hold the male element 711 and female element 713, respectively, in a formation for cutting. With reference to FIG. 15, the male element 711 has been received by the female element 713, as shown in FIG. 14, and further depicted are caps 911 and 913 for holding male element 711 and female element 713, respectively, in a formation for cutting. Male element 711 and female element 713, as well as caps 911 and 913, are situated coaxially around tube 918.

Another embodiment for the method for improving transcatheter aortic valve implantation is shown in FIGS. 6A and 7B, which encompasses the preferred embodiment with additional features. This method includes inserting a device 750 through a native aortic valve 526, wherein the device has a filter umbrella 715 and a punch having a male element 711 and a female element 713 separable along a plane perpendicular to connection. The device is inserted transapically in FIG. 6A, through the apex 116 of the heart into the left ventricle 118 and up through the aortic valve 102 and into the aorta 101. However, the device may be inserted transapically, transaortically, or transfemorally.

The arrangement of elements of the device must change due to direction of bloodflow when the device is inserted transaortically or transfemorally, as compared to transapically. A suitable embodiment of a device 700 for use in inserting via the aorta or femoral artery is show in FIG. 19A. The primary difference between the device when inserted transaortically or transfemorally, as opposed to transapical insertion, is the orientation of the filter umbrella 715 and punch 902. As the filter umbrella 715 is used to catch any debris, including calcium buildup that is dislodged during perforation of the native aortic valve, and blood flows out of the left ventricle into the aorta through the aortic valve, the filter umbrella must be positioned in the aorta downstream of the aortic valve. In transaortic and transfemoral insertion, the filter umbrella 715 is therefore positioned behind the punch 902 along the device 700 or proximal to the user of the device relative to the punch 902, as demonstrated in FIG. 19A. In contrast, the transapical device 750 is oriented such that the filter umbrella 712 is positioned in front of the punch 902, or distal to the user of the device 750 relative to the punch 902 as shown in FIGS. 6A and 7B.

The method then includes positioning the filter umbrella 712 in an aorta down-stream of the aortic valve. The filter umbrella is disengaged, or closed, during insertion to prevent any accidental damage to surrounding tissue or dislodgement of calcium deposits, similar to the punch 902. This is achievable through a slidable cover 705 as shown in FIG. 7B for transapical devices, or a slidable cover 705 as shown in FIG. 7A for transaortic or transfemoral devices.

A further step is engaging the filter umbrella 712 such that the filter umbrella 712 allows blood to pass beyond the aorta, but catches dislodged calcium particles to prevent such particles from passing through the rest of the body via the aorta. This step is achievable via the slidable cover 705 sliding and releasing the filter umbrella 715 such that the filter umbrella 715 is allowed to expand circumferentially to encompass the circumference of the aorta. Expansion of the filter umbrella 715 is achieved by operating spindle 708 to slide and release the filter umbrella 715, as shown in FIGS. 16A, 16B, 16C, and 27.

Another step includes opening the punch 902 within the native aortic valve 526 such that aortic valve leaflets 528 are positioned between the cutting edge 711a of the male element 711 and the cutting edge 713a of the female element 713. FIGS. 22C and 22D are exploded views of spindles 702 and 706, respectively, which operate the removal of covers 701 and 703 to open the male 711 and female 713 elements of the punch 902. FIG. 22B shows the punch 902 opened to position the aortic leaflets between the male 711 and female 713 elements, and FIG. 22A illustrates the overall operation of device 700.

A next step includes closing the punch 902 over the aortic valve leaflets 528 so that the male element 711 applies force along the cutting edge 711a to a superior surface of the aortic valve leaflets 528 and the female element 713 applies force along the cutting edge 713a to an inferior surface of the aortic valve leaflets 528. FIG. 20B demonstrates the closing of the punch 902.

The final step includes leaving a ring of calcium deposits 246 along the circumference of the native aortic valve 526. The perforation of the native aortic valve 526 should leave a circumferential ring of the remaining tissue of the native aortic valve with a preferable length of 2-3 millimeters. Further, the perforation is preferably centered such that the resulting circumferential ring of tissue is uniform in radial length. As previously explained, a semi-rigid ring composed of the remaining aortic heart is useful in stabilizing any TAVI replacement valve during and after insertion. Additionally, less radial pressure is ultimately placed on the heart conduction system as the majority of the calcium deposits are removed from the native aortic valve. Further, the chance of paravalvular leaks is reduced, as the shortened aortic leaflets make insertion of replacement valves easier and more successful.

Figures 16A, 16B, 16C:
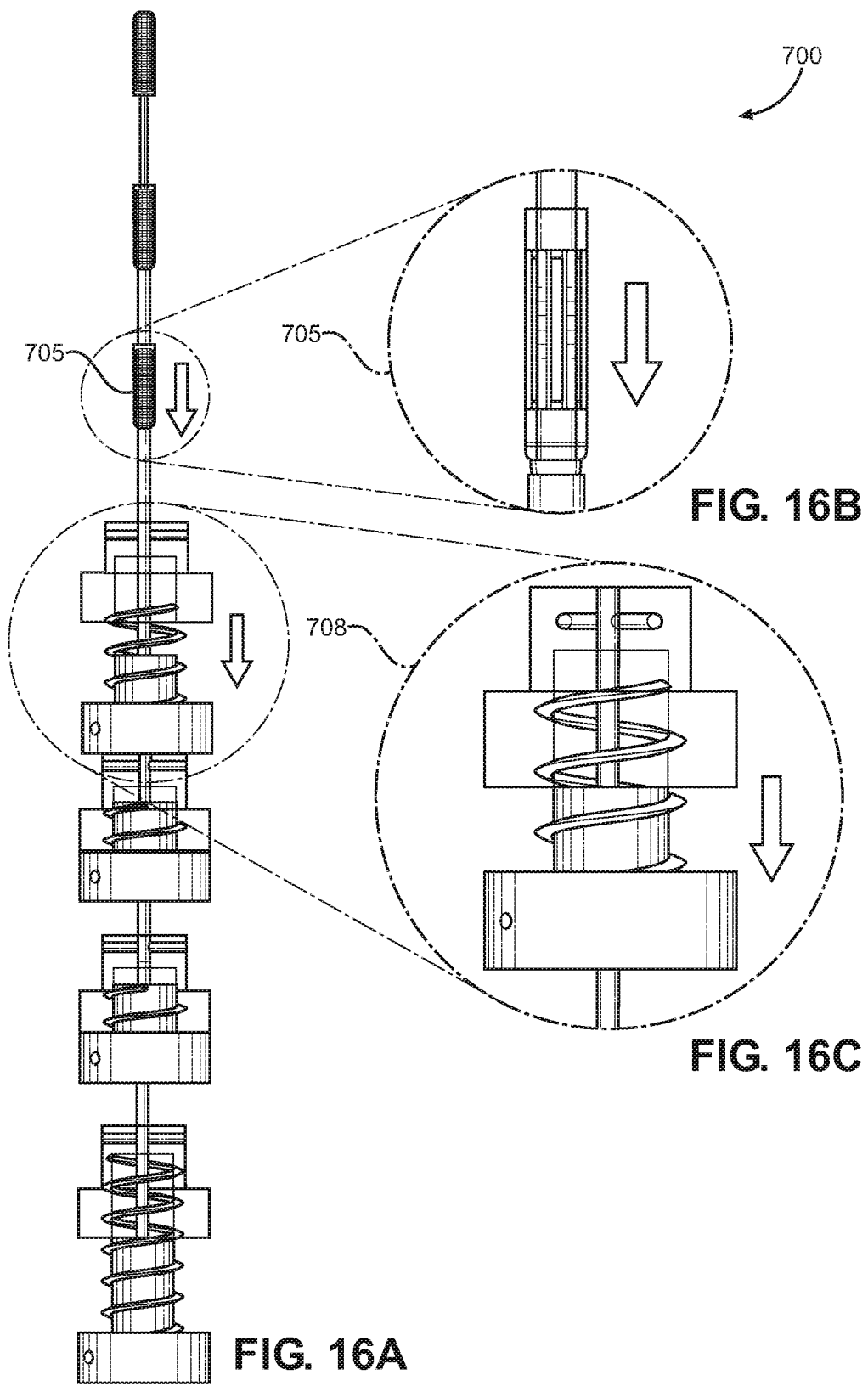
FIG. 16A shows an exemplary embodiment of the totally percutaneous collapsible aortic punch device in accordance with the present invention.
FIG. 16B shows an exploded view of a cover in the totally percutaneous collapsible aortic punch device in accordance with the present invention.
FIG. 16C shows an exploded view of a spindle in the totally percutaneous collapsible aortic punch device in accordance with the present invention.

With reference to FIG. 16A, the device 700 is shown with detailed views of the cover 705 that compresses the filter umbrella 715, and spindle 708 for controlling the cover 705. FIG. 16B shows an exploded view of cover 705, and FIG. 16C shows an exploded view of spindle 708. The down arrows indicate operation of the spindle 708 to remove the cover 705.

With reference to FIG. 17A, the device 700 is shown with detailed views of the cover 701 that compresses the male element 711, the cover 703 that compresses the female element 713, and spindle 704. FIG. 17B shows an exploded view of cover 701, FIG. 17C shows and exploded view of cover 703, and FIG. 17D shows an exploded view of spindle 704. The spindle 704 controls the distance between cover 701 and cover 703.

With reference to FIG. 18A, device 700 is shown. With reference to FIG. 18C, an exploded view of spindle 702 for controlling cover 701 is illustrated with a downward arrow indicating an operation to retract cover 701 that corresponds to FIG. 18B. With reference to FIG. 18E, an exploded view of spindle 706 for controlling cover 703 is illustrated with a upward arrow indicating an operation to retract cover 703 that corresponds to FIG. 18D. FIG. 18F shows the 902 in an uncompressed state.

Figure 19B:
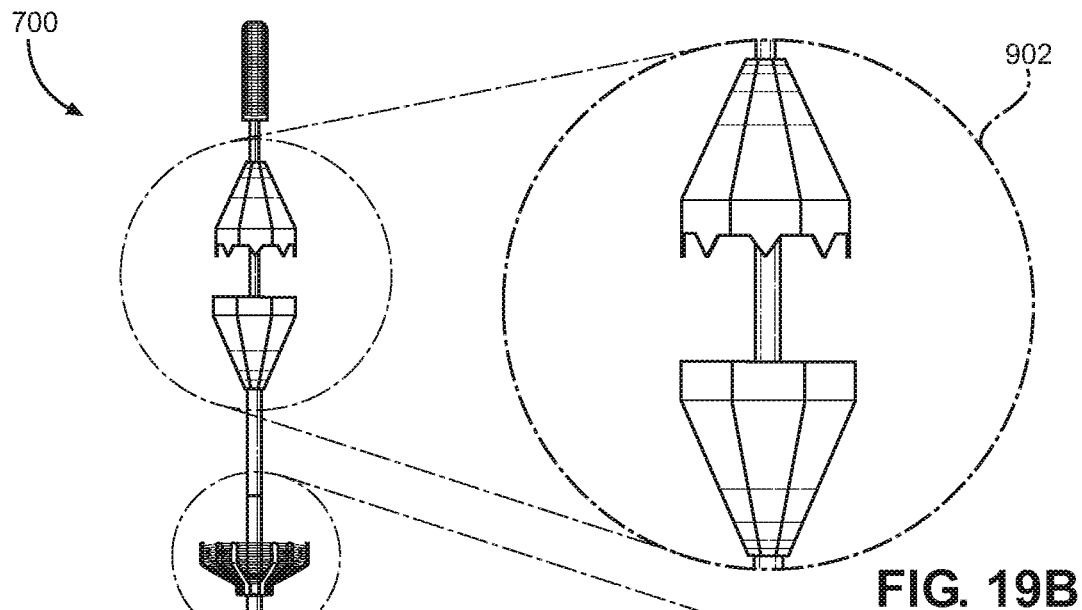
FIG. 19B shows an exploded view of an open totally percutaneous collapsible punch in accordance with the present invention.
Figure 19C:
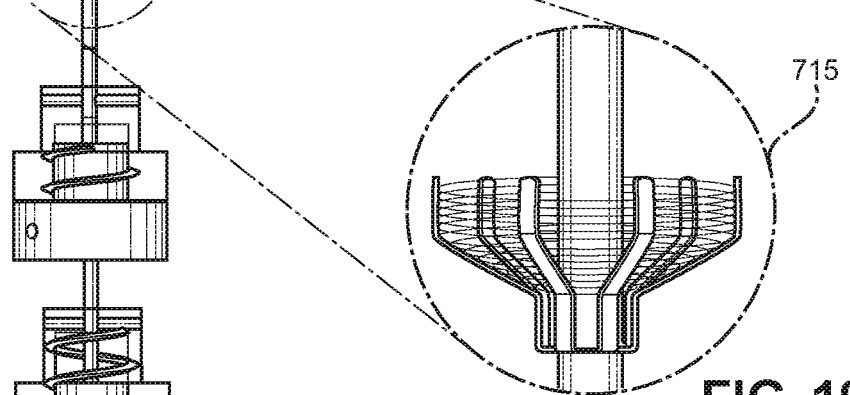
FIG. 19C shows is an exploded view of a filter umbrella in accordance with the present invention.
Figure 19A:
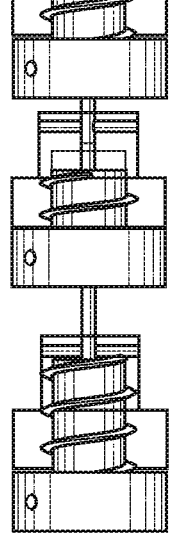
FIG. 19A shows an exemplary totally percutaneous collapsible aortic punch device in accordance with the present invention.

With reference to FIG. 19A, device 700 is shown. FIG. 19B illustrates an exploded view of the punch 902. FIG. 19C illustrates an exploded view of the filter umbrella 718.

Figure 21B:
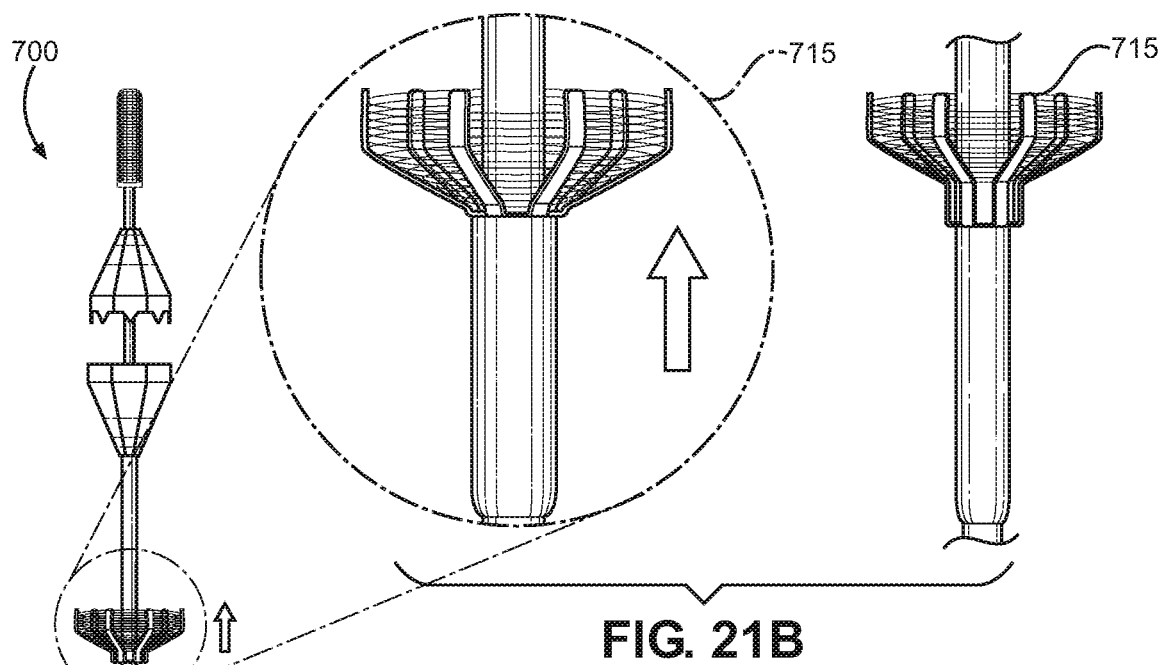
FIG. 21B shows is an exploded view of a filter umbrella in accordance with the present invention.
Figure 21C:
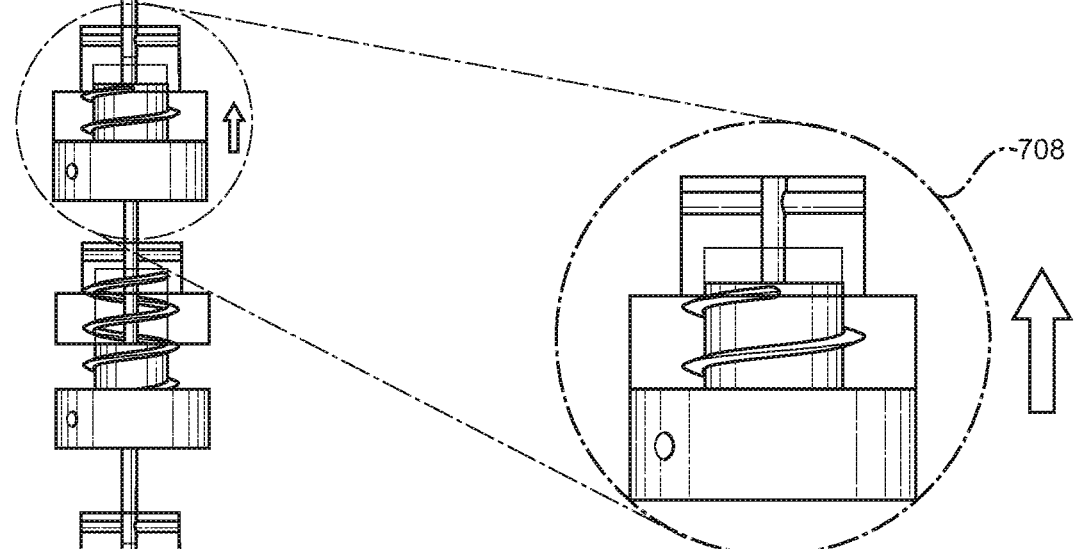
FIG. 21C shows an exploded view of a spindle in the totally percutaneous collapsible aortic punch device in accordance with the present invention.
Figure 21A:
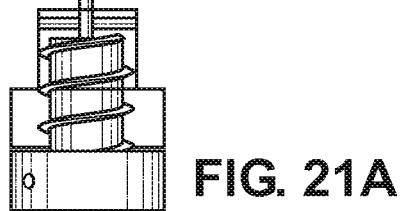
FIG. 21A shows an exemplary totally percutaneous collapsible aortic punch device in accordance with the present invention.

With reference to FIG. 21A, device 700 is shown. FIG. 21B is an exploded view of the filter umbrella 715 in an uncompressed formation. FIG. 21C is an exploded view of the spindle 708 for controlling the decompression of the filter umbrella 715, as indicated by the upward arrows.

Figure 23:
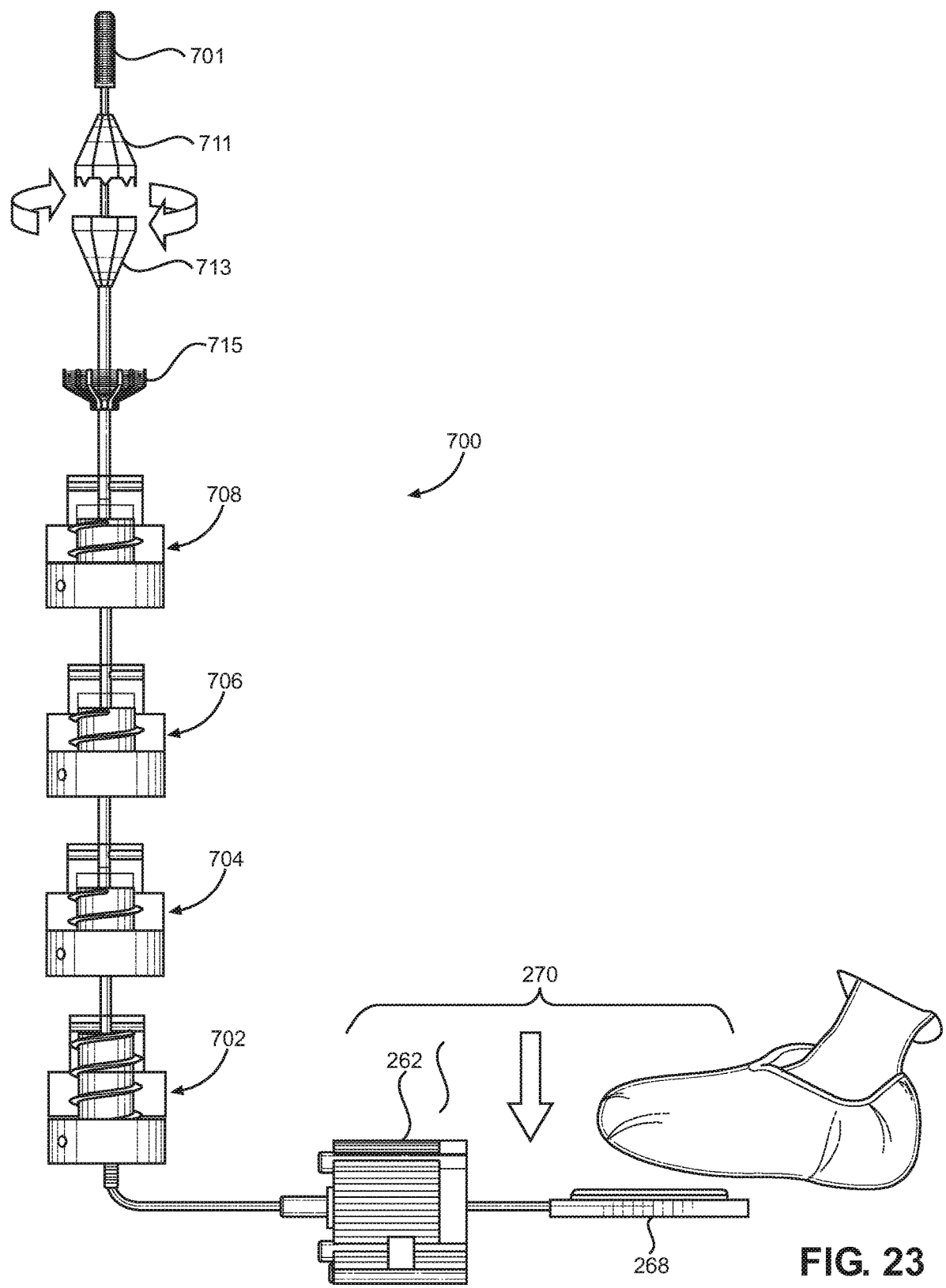
FIG. 23 shows an exemplary totally percutaneous collapsible aortic punch device with a motor in accordance with the present invention.
Figure 24:
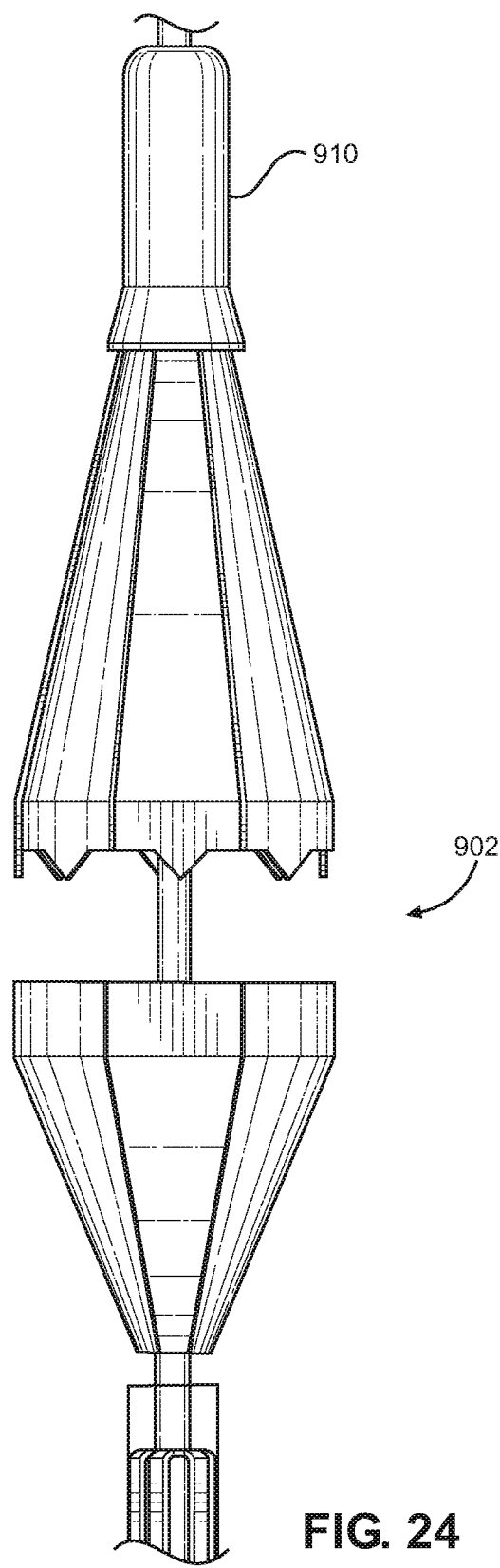
FIG. 24 shows the open male and female elements of the punch device in accordance with the present invention.

There are multiple embodiments for removing calcium deposits from aortic valves. An embodiment of a device 700 for improving transcatheter aortic valve implantation is shown in FIG. 7A. As shown in FIG. 24, the punch 902 may have a tip 910 attached to or formed by a male element 711. As shown in FIGS. 20A and 23, the spindle 704 is configured to turn either clockwise or counterclockwise to raise and lower the male element 711 via the tube 718 relative to the female element 713. The action of raising and lowering the male element 711 allows the device to perforate biological tissue, specifically, valve leaflets.

The punch 902 can be made of medical grade plastics or metals, as typically used in similar invasive devices. At least the male element 711 has a cutting edge 711a used to perforate an aortic leaflet or other biological tissue. The cutting edge 711a is typically located around a circumference of the male element 711, and can be shaped in different manners, including, but not limited to, a uniform circle about a plane, a plurality of teeth in sine wave, square, triangle, or sawtooth pattern, or similar orientation.

The female element 713 can also have a cutting element 713a shaped to accept the pattern of the male cutting element 711a. The female element 713 may likewise contain a receptacle for accepting the male cutting element 711a.

The device 700 may further include a motor assembly 270, as shown in FIG. 23, used to rotatably close the punch 902, in addition to the punch control spindle 704. The motor assembly 270 includes an operator control element 268 attached to a high speed motor 262, which is attached to the male element 711 a cable (not shown). The motor assembly 270 can only close the punch 902, whereas the punch control spindle 704 can both open and close the punch 902. The operator control element 268 activates and deactivates the high speed motor 262, and may be in the form of a foot pedal as seen in FIG. 23, but may also include a button, a hand-held pedal, or other similar device. The cable, attached at one end to the male element 711 and at an opposite end to the high speed motor 262, must be of a variable length, such that the male element may be pulled down to the female element 713 to form a fusiform punch 902 and then pushed up via the punch control element 704 to separate the male element from the female element.

Figure 26:
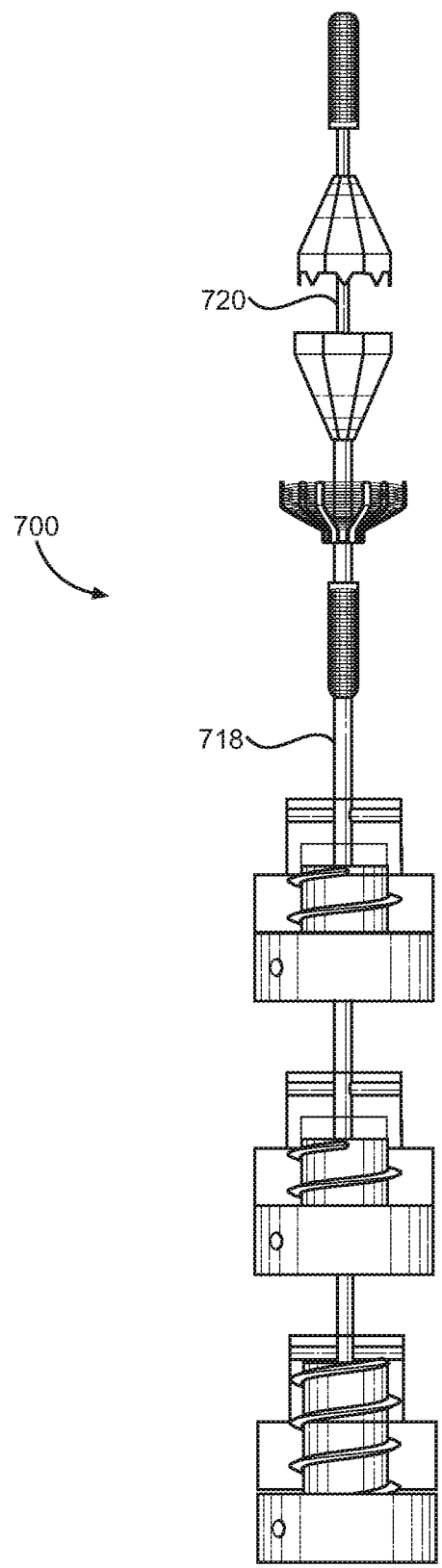
FIG. 26 shows an exemplary totally percutaneous collapsible aortic punch device in accordance with the present invention.

FIG. 26 illustrates device 700 wherein tube 718 is wrapped coaxially around secondary tube 720 that extends from the proximal center of female element to the distal end of device 700, extending through the center of female element 713 and female element 713, and may actuate operation of the punch 902 such that the male element and female element 713 are controlled to advance and retreat relative to one another using a cable (not shown) connected to spindle 704 that extends through secondary tube 720.

While the invention has been shown and described with reference to certain exemplary embodiments thereof, it will be understood by those skilled in the art that various changes in form and details may be made therein without departing from the spirit and scope of the invention as defined by the appended claims and their equivalents.

I claim:

1. A totally percutaneous device for removing calcium deposits from an aortic valve, comprising:
 a punch system including a collapsible male element positioned coaxially around at a distal end of a primary tube and spaced apart from a collapsible female element positioned coaxially around the primary tube proximal to the male element;
 a collapsible filter umbrella positioned coaxially around the primary tube proximal to the female element;
 a first removable cover positioned coaxially around the primary tube for covering and uncovering the collapsible male element such that the male element is collapsed when covered by the first removable cover;
 a second removable cover positioned coaxially around the primary tube for covering and uncovering the collapsible female element such that the female element is collapsed when covered by the second removable cover;
 a third removable cover positioned coaxially around the primary tube for covering and uncovering the collapsible filter umbrella such that the filter umbrella is collapsed when covered by the third removable cover; and
 a control system positioned at a proximal end of the primary tube and controlling the first removable cover, second removable cover, and third removable cover to cover and uncover the male element, the female element, and the filter umbrella, respectively,
 wherein the control system includes a punch control driver actuating the uncollapsed male element and the uncollapsed female element to advance and retreat relative to one another within the aortic valve.

2. The device of claim 1, wherein the male element has teeth positioned along a circumferential edge of a proximal end of the male element, and the female element has grooves positioned along a circumferential edge of a distal end of the female element positioned to accept the teeth of the male element.

3. The device of claim 1, further comprising a motor assembly attached to the male element, wherein the motor assembly includes a high speed motor attached to the male element via a cable and an operator control element is attached to the high speed motor, and wherein the operator control element is configured to activate or deactivate the high speed motor, which when activated rotatably closes the male element against the female element.

4. A totally percutaneous device for removing calcium deposits from an aortic valve, comprising:
 a collapsible filter umbrella positioned coaxially around at a distal end of a primary tube;
 a punch system including a collapsible female element positioned coaxially around the primary tube proximal to the filter umbrella and spaced apart from a collapsible male element positioned coaxially around the primary tube proximal to the female element;
 a first removable cover positioned coaxially around the primary tube for covering and uncovering the collapsible male element such that the male element is collapsed when covered by the first removable cover;
 a second removable cover positioned coaxially around the primary tube for covering and uncovering the collapsible female element such that the female element is collapsed when covered by the second removable cover;
 a third removable cover positioned coaxially around the primary tube for covering and uncovering the collapsible filter umbrella such that the filter umbrella is collapsed when covered by the third removable cover; and
 a control system positioned at the proximal end of the primary tube and controlling the first removable cover, second removable cover, and third removable cover to cover and uncover the male element, the female element, and the filter umbrella, respectively,
 wherein the control system includes a punch control driver actuating the uncollapsed male element and the uncollapsed female element to advance and retreat relative to one another within the aortic valve.

5. The device of claim 4, wherein the male element has teeth positioned along a circumferential edge of a proximal end of the male element and the female element has grooves positioned along a circumferential edge of a distal end of the female element positioned to accept the teeth of the male element.

6. The device of claim 4, further comprising further comprising a motor assembly attached to the male element, wherein the motor assembly includes a high speed motor attached to the male element via a cable and an operator control element is attached to the high speed motor, and wherein the operator control element is configured to activate or deactivate the high speed motor, which when activated rotatably closes the male element against the female element.

7. A method of a totally percutaneous aortic punch for removing calcium deposits from an aortic valve, comprising:
inserting a device through an aortic valve, wherein the device has a collapsible filter umbrella positioned coaxially around a primary tube for catching debris from operation of the device and a collapsible punch system for perforating the aortic valve;
positioning the punch system within the native aortic valve, wherein a collapsible male element and a collapsible female element of the punch system are collapsed to avoid inadvertent damage to surrounding tissue, and wherein the male element and female element are on positioned on opposite sides of native aortic valve;
positioning the filter umbrella, while collapsed, in an aorta down-stream of blood flow through the aortic valve, such that the filter umbrella allows blood to pass beyond the aorta and catches debris;
uncompres sing the collapsed male element, female element, and filter umbrella;
perforating the aortic valve to remove calcium deposits from the aortic valve; and
leaving a ring of calcium deposits along the circumference of the native aortic valve,
wherein the device further includes
a first removable cover positioned coaxially about the device for covering and uncovering the male element such that the male element is collapsed when covered by the first removable cover;
a second removable cover positioned coaxially about the device for covering and uncovering the female element such that the female element is collapsed when covered by the second removable cover;
a third removable cover positioned coaxially about the device for covering and uncovering the filter umbrella such that the filter umbrella is collapsed when covered by the third removable cover; and
a control system positioned at a proximal end of the primary tube and controlling the first removable cover, the second removable cover, and the third removable cover to cover and uncover the male element, the female element, and the filter umbrella, respectively.

8. The method of claim 7, wherein the device is inserted through the native aortic valve transapically.

9. The method of claim 7, wherein the device is inserted through the native aortic valve transfemorally or transaortically.

10. The method of claim 7,
wherein the control system includes a punch control driver actuating one or both of the male element and the female element to advance and retreat relative to one another along a length of the device.

11. The method of claim 10, wherein the male element has teeth positioned along a circumferential edge of a proximal end of the male element, and the female element has grooves positioned along a circumferential edge of a distal end of the female element positioned to accept the teeth of the male element.

12. A collapsible punch system for totally percutaneous removal of calcium deposits from an aortic valve, comprising:
a male element having a center ring and a plurality of symmetrical spokes increasing in width toward a common circumference, the male element being deformable to a closed conical shape in which the spokes form a continuous ring at the circumference, wherein the spokes are collapsible to a cylinder shape when compressed and return to the conical shape when uncompressed;
a female element having a center ring and a plurality of symmetrical spokes increasing in width toward a common circumference, the female element being deformable to a closed conical shape in which the spokes form a continuous ring at the circumference, wherein the spokes are collapsible to a cylinder shape when compressed and return to the conical shape when uncompressed; and
a punch control element configured to move the collapsible male element in relation to the collapsible female element when the male element and the female element are uncompressed,
wherein the female element receives the male element, and
wherein ends of the spokes of the male element form a cutting edge at the circumference of the conical shape.

13. The device of claim 12, wherein the cutting edge forms a uniform circle about a plane or a plurality of teeth in one of a sine wave, square, triangle, or sawtooth pattern.

14. The device of claim 12, wherein the male element and the female element are formed of nitinol.

15. The device of claim 12, wherein the male element and the female element are formed of a shape memory alloy.

16. The device of claim 12, wherein ends of the spokes of the female element form a cutting edge at the circumference of the conical shape.

* * * * *